US009433671B2

(12) United States Patent
Powell

(10) Patent No.: US 9,433,671 B2
(45) Date of Patent: Sep. 6, 2016

(54) ANTI-MALARIA COMPOSITIONS AND METHODS

(71) Applicant: ARTIFICIAL CELL TECHNOLOGIES, INC., New Haven, CT (US)

(72) Inventor: Thomas J. Powell, Madison, CT (US)

(73) Assignee: ARTIFICIAL CELL TECHNOLOGIES, INC., New Haven, CT (US)

( * ) Notice: Subject to any disclaimer, the term of this patent is extended or adjusted under 35 U.S.C. 154(b) by 0 days.

(21) Appl. No.: 13/827,469

(22) Filed: Mar. 14, 2013

(65) Prior Publication Data

US 2013/0259945 A1    Oct. 3, 2013

Related U.S. Application Data

(60) Provisional application No. 61/617,998, filed on Mar. 30, 2012.

(51) Int. Cl.

| A61K 39/002 | (2006.01) |
|---|---|
| A61K 9/70 | (2006.01) |
| A61K 9/50 | (2006.01) |
| A61K 39/015 | (2006.01) |
| A61K 39/00 | (2006.01) |

(52) U.S. Cl.
CPC ............. *A61K 39/002* (2013.01); *A61K 9/50* (2013.01); *A61K 9/7007* (2013.01); *A61K 39/015* (2013.01); *A61K 2039/55555* (2013.01)

(58) Field of Classification Search
None
See application file for complete search history.

(56) References Cited

U.S. PATENT DOCUMENTS

| 5,723,130 | A | 3/1998 | Hancock et al. |
|---|---|---|---|
| 7,045,146 | B2 | 5/2006 | Caruso et al. |
| 7,615,530 | B2 | 11/2009 | Haynie |
| 7,723,294 | B2 | 5/2010 | Haynie |
| 7,807,634 | B2 * | 10/2010 | Haynie .................. 514/4.4 |
| 7,923,560 | B2 | 4/2011 | Wightman et al. |
| 7,939,103 | B2 | 5/2011 | Dahne et al. |
| 8,092,836 | B2 | 1/2012 | Donath et al. |
| 2005/0069950 | A1 | 3/2005 | Haynie |
| 2008/0233143 | A1 | 9/2008 | Jackson et al. |
| 2009/0035323 | A1 | 2/2009 | Stoermer et al. |
| 2009/0239378 | A1 | 9/2009 | Kashefizadeh et al. |
| 2009/0304756 | A1 | 12/2009 | Dahne et al. |
| 2010/0028423 | A1 | 2/2010 | Haynie |
| 2010/0158928 | A1 | 6/2010 | Stoermer et al. |
| 2010/0247599 | A1 | 9/2010 | Krohne et al. |
| 2015/0030682 | A1 | 1/2015 | Powell et al. |

FOREIGN PATENT DOCUMENTS

| WO | 2009082440 A2 | 7/2009 |
|---|---|---|
| WO | 2012006395 A1 | 1/2012 |

OTHER PUBLICATIONS

Phelps et al. Langmuir, 2011, 27(3), pp. 1123-1130.*
Calva-Calle et al.; "A Linear Peptide Containing Minimal T- and B-Cell Epitopes of Plasmodium falciparum Circumsporozoite Protein Elicits Protection against Transgenic Sporozoite Challenge"; Infection and Immunity; pp. 6929-6939; (2006).
Chong et al.; "A Paradigm for Peptide Vaccine Delivery Using Viral Epitopes Encapsulated in Degradable Polymer Hydrogel Capsules"; Biomaterials; 30; pp. 5178-5186; (2009).
Kumar et al.; "Quantitative Plasmodium Sporozoite Neutralization Assay (TSNA)" Journal of Immunological Methods; 292; pp. 157-164; (2004).
Moreno et al.; "CD4+ Cell Clones Obtained from Plasmodium Falciparum Sporozoite-Immunized Volunteers Recognize Polymorphic Sequences of the Circumsporozoite Protein"; The Journal of Immunology; 151; pp. 489-499; (1993).
Nardin et al.; "Conserved Repetitive Epitope Recognized by CD4+ Clones from a Malaria-Immunized Volunteer"; Reports; 246; pp. 1603-1606; (2009), Science Journal.
Persson et al.; "Cutting Edge: A New Tool to Evaluate Human Pre-Erythrocytic Malaria Vaccines: Rodent Parasites Bearing a Hybrid Plasmodium falciparum Circumsporozoite Protein"; The Journal of Immunology; 169; pp. 6681-6685; (2002).
Powell et al.; "Synthetic Nanoparticles Vaccines Produced by Layer-by-Layer Assembly of Artificial Biofilms Induce Potent Protective T-cell and Antibody Responses in Vivo"; Vaccine; 29; pp. 558-569; (2011).
Powell et al., "Plasmodium Falciparum Synthetic LbL Microparticle Vaccine Elicits Protective Neutralizing Antibody and Parasite-Specific Cellular Immune Responses"; Vaccine; 31; pp. 1898-1904; (2013).
Moon et al.; "Antigen-Displaying Lipid-Enveloped PLGA Nanoparticles as Delivery Agents for a Plasmodium vivax Malaria Vaccine"; PLOS ONE; 7(2); pp. 1-17; (2012).
International Search Report and Written Opinion; International Application No. PCT/US2013/033070; International Filing Date Mar. 20, 2013; Date of Mailing Jun. 18, 2013; 13 pages.
Blander et al.; "Toll-dependent Selection of Microbial Antigens for Presentation by Dendritic Cells"; Nature; 440; pp. 808-812 (2006).

(Continued)

*Primary Examiner* — Oluwatosin Ogunbiyi

(74) *Attorney, Agent, or Firm* — Cantor Colburn LLP

(57) ABSTRACT

Multilayer films comprise polypeptide epitopes from *Plasmodium falciparum*, specifically a circumsporozoite T1, B or T* epitope. The multilayer films are capable of eliciting an immune response in a host upon administration to the host. The multilayer films can include at least one designed peptide that includes one or more polypeptide epitopes from a *Plasmodium* protozoan.

19 Claims, 9 Drawing Sheets

(56) References Cited

OTHER PUBLICATIONS

Blander, J. Magarian; "Phagocytosis and Antigen Presentation: a Partnership Initiated by Toll-like Receptors"; Ann Rheum Dis; 67; pp. iii44-iii49; (2008).

Cyr et al.; "C57B1/6 Mice are Protected From Respiratory Syncytial Virus (RSV) Challenge and IL-5 Associated Pulmonary Eosinophilic Infiltrates Following Intranasal Immunization with Protollin-eRSV Vaccine"; Vaccine 25; pp. 3228-3232; (2007).

Cyr et al.; "Intranasal Proteosome-based Respiratory Syncytial Virum (RSV) Vaccines Protect BALB/c Mice Against Challenge Without Eosinophilia or Enhanced Pathology"; Vaccine; 25; pp. 5378-5389; (2007).

De Haes et al.; "Polyelectrolyte Capsules-Containing HIV-1 p24 and Poly I:C Modulate Dendritic Cells to Stimulate HIV-1-specific Immune Responses"; Molecular Therapy 18(7); pp. 1408-1416; (2010).

Demento et al.; "Inflammasome-Activating Nanoparticles as Modular Systems for Optimizing Vaccine Efficacy"; Vaccine; 27; pp. 3013-3021; (2009).

DeMuth et al.; "Releasable Layer-by-Layer Assembly of Stabilized Lipid Nanocapsules on Microneedles for Enhanced Transcutaneous Vaccine Delivery"; ACS NANO; 6(9); pp. 8041-8051; (2012).

Hancock et al.; "Adjuvants Recognized by Toll-like Receptors Inhibit the Induction of Polarized Type 2 T Cell Responses by Natural Attachment (G) Protein of Respiratory Syncytial Virus"; Vaccine; 21; pp. 4348-4358; (2003).

Hill et al.; "Vaccines Against Malaria"; Phil. Trans. R. Soc. B.; 366; pp. 2806-2814; (2011).

Nardin et al.; "A Totally Synthetic Polyoxime Malaria Vaccine Containing Plasmodium Falciparum B Cell and Universal T Cell Epitopes Elicits Immune Responses in Volunteers of Diverse HLA Types"; The Journal of Immunology, The American Association of Immun.

Stanisic et al.; "Escaping the Immune System: How the Malaria Parasite Makes Vaccine Development a Challenge"; Trends in Parasitology; 29(12); pp. 612-622; (2013).

Su et al.; "Layer-by-Layer-Assembled Multilayer Films for Transcutaneous Drug and Vaccine Delivery"; ACS NANO; 3 (11); pp. 3719-3729; (2009).

\* cited by examiner

ANTI-MALARIA COMPOSITIONS AND METHODS

CROSS-REFERENCE TO RELATED APPLICATION

This application claims priority to U.S. Provisional Application Ser. No. 61/617,998 filed on Mar. 30, 2012, which is incorporated herewith in its entirety.

FIELD OF THE DISCLOSURE

The present disclosure relates to compositions and methods for the prevention of malaria infections, specifically multilayer film compositions containing antigenic epitopes.

BACKGROUND

Malaria is one of the most prevalent infections in tropical and subtropical areas throughout the world. Malaria infections lead to severe illnesses in hundreds of millions of individuals worldwide, leading to death in millions of individuals, primarily in developing and emerging countries every year. The widespread occurrence and elevated incidence of malaria are a consequence of the increasing numbers of drug-resistant parasites and insecticide-resistant parasite vectors. Other factors include environmental and climatic changes, civil disturbances, and increased mobility of populations.

Malaria is caused by the mosquito-borne hematoprotozoan parasites belonging to the genus *Plasmodium*. Four species of *Plasmodium* protozoa (*P. falciparum, P. vivax, P. ovale* and *P. malariae*) are responsible for the disease in man; many others cause disease in animals, such as *P. yoelii* and *P. berghei* in mice. *P. falciparum* accounts for the majority of infections and is the most lethal type, sometimes called "tropical malaria". Malaria parasites have a life cycle consisting of several stages. Each stage is able to induce specific immune responses directed against the corresponding occurring stage-specific antigens.

There is a need for improved antigenic compositions suitable for stimulating an immune response to malaria.

SUMMARY

In one aspect, a composition comprises a first multilayer film comprising a plurality of oppositely charged polyelectrolyte layers, wherein one of the polyelectrolyte layers in the multilayer film comprises a first antigenic polyelectrolyte, wherein the first antigenic polyelectrolyte comprises a *Plasmodium falciparum* circumsporozoite T1, B or T* epitope covalently linked to a first polyelectrolyte, and wherein the polyelectrolytes in the multilayer film comprise a polycationic material or a polyanionic material having a molecular weight of greater than 1,000 and at least 5 charges per molecule.

In another embodiment, a composition comprises a first multilayer film comprising a plurality of oppositely charged polyelectrolyte layers, wherein one of the polyelectrolyte layers in the multilayer film comprises a first antigenic polypeptide, wherein the first antigenic polypeptide comprises a *Plasmodium falciparum* circumsporozoite T1, B and T* epitopes covalently linked to a first polypeptide, and wherein the polyelectrolytes in the multilayer film comprise a polycationic material or a polyanionic material having a molecular weight of greater than 1,000 and at least 5 charges per molecule.

BRIEF DESCRIPTION OF THE DRAWINGS

FIG. 1 shows the epitopes and designed peptides for circumsporozoite peptide-containing nanoparticles. (Top panel) Diagram of *P. falciparum* CS protein showing locations and sequences of T1, B, and T* epitopes. (Bottom panel) Design of CS subunit peptides fused to a poly-lysine tail.

FIGS. 2 and 3 show antibody responses following immunization with nanoparticles containing malaria CS epitopes. BALB/c (FIG. 2) and C57BL/6 (FIG. 3) mice (3/group, 5-6 weeks old) were immunized on days 0, 21 and 42. On day 28, mice were bled and pooled sera were tested for T1BT*-specific IgG titers by ELISA.

FIG. 4 shows the antigenicity of malaria nanoparticles. An ELISA plate was coated with the nanoparticles indicated in the legend and probed with serial dilutions of the NANP-specific mAb 2A10. Following incubation with HRP-conjugated secondary antibodies, plate was developed with Ultra TMB substrate. The results reflect the mean±SD OD450 of triplicate samples.

FIGS. 5 and 6 show T-cell responses induced by CS LbL nanoparticles in BALB/c (FIG. 5) and C57BL/6 (FIG. 6) mice. Mice were immunized as indicated. Spleen cells were harvested on day 49, enriched for CD4+ or CD8+ cells, and restimulated with T* or T1 in ELISPOT plates. Results show mean±SD for 3 mice per group.

FIG. 7 shows T-cell responses elicited by nanoparticles containing malaria CS epitopes. Spleens from mice immunized with T1BT* peptide or nanoparticle then challenged with PfPb were tested in IL-5 and IFNγ ELISPOT against T1BT* (Panel A) or T1 (Panel B) peptides. Data depict mean±SD of 7 mice per group.

FIG. 8 shows parasite RNA levels in livers of challenged mice. RNA was extracted from the livers of the PfPb-challenged mice reported in FIG. 7 and analyzed for parasite burden by qPCR. The results show parasite rRNA copy number per liver RNA sample in individual mice. Gray bars depict >90% (1-log) reduction in parasite rRNA copy number compared to the average of the seven PBS-treated mice; stippled light gray bars represent >80% reduction compared to PBS average.

FIG. 9 shows immunogenicity and efficacy of LbL microparticles containing malaria T1BT* epitopes. C57BL/6 mice were immunized on days 0 and 21 as indicated. Sera were collected on day 28 and tested for T1B-specific IgG titers by ELISA and functional antibodies by TSNA. Results show mean±SD of 5 mice per group for antibody titer (grey bar) and % inhibition (red bar); pooled sera from 5 mock-immunized (PBS) mice were used for both assays. * $P<0.05$ for ELISA compared to 1140; ** $P<0.05$ for ELISA and TSNA compared to 1140.

FIG. 10 shows T-cell responses of mice depicted in FIG. 9. On day 28, spleen cells were collected and restimulated with T1BT* peptide in IFNγ and IL-5 ELISPOT plates, and the number of spot-forming cells on each plate was counted in an AID ViruSpot Reader. Results show mean±SD of 3 mice per group.

FIG. 11 shows protective efficacy in mice immunized with LbL microparticles containing T1BT* epitopes. C57BL/6 mice were immunized on days 0, 21, and 42, and challenged on day 56. Parasite burden in the livers was measured by qPCR 2 days post-challenge. Results show parasite rRNA copy number of individual mice (gray circles) and mean value for each group (red bars); insets show number of mice per group that were protected (>90% reduction of parasite rRNA), group % reduction of parasite rRNA, and * P<0.05, all compared to PBS control group; NS=not significant.

Figure 11:
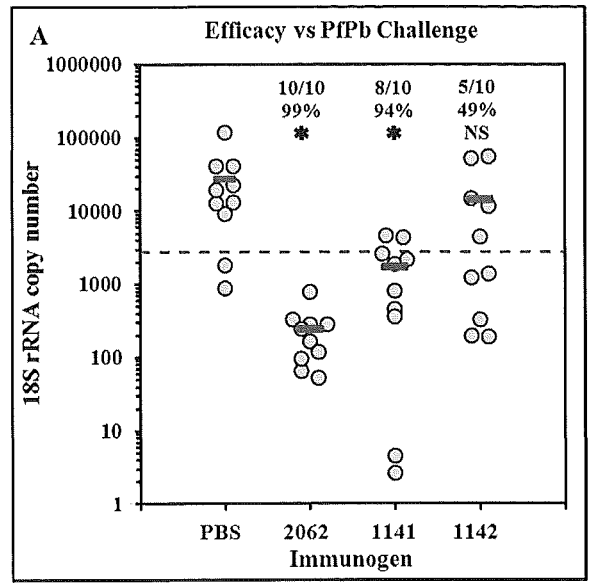
Figure 14:
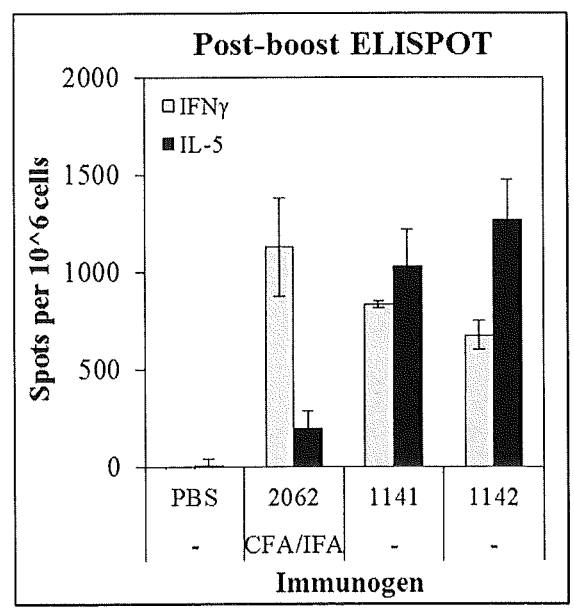

FIG. 14 shows T-cell responses of mice depicted in FIG. 11. Mice were immunized with the indicated treatments on days 0, 21 and 42 (peptide 2062 in CFA and IFA, respectively). Spleen cells were harvested on day 49 and restimulated with T1BT* peptide in IFNγ and IL-5 ELISPOT plates. The data depict the mean±SD of 3 mice per group.

Figure 15:
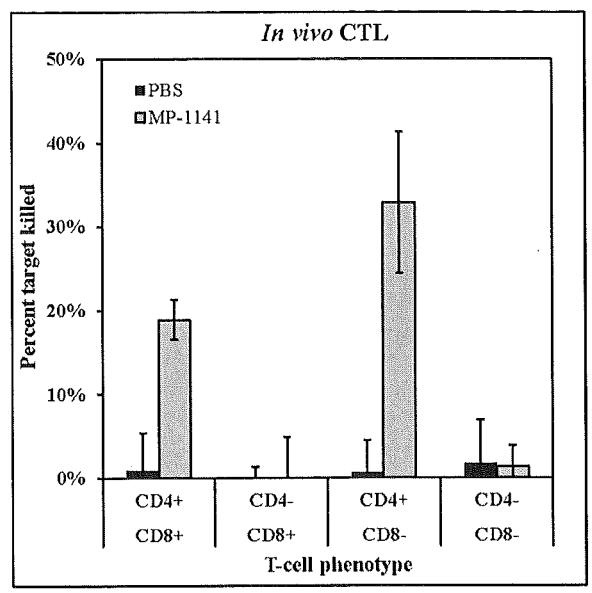

FIG. 15 shows cellular immunity induced by LbL microparticles containing malaria T1BT* epitopes. BALB/c mice were mock-immunized with PBS or immunized with MP-1141, and 7 days later were depleted of CD4+ or CD8+ cells or both. In vivo CTL activity was measured the day following depletion. Results show mean±SD percent peptide-specific killing in 3 mice per group. X-axis shows phenotype of T-cells remaining in the mice on day of challenge.

FIG. 16 shows cellular immunity induced by LbL microparticles containing malaria *P. berghei* CS epitopes. BALB/c mice were immunized on days 0 and 28 with DP 2147 (Pb CD4+:CD8+ fusion peptide) in Freund's adjuvant or MP loaded with Pb CD4+ peptide (MP-1182), CD8+ peptide (MP-1183) or CD4+:CD8+ fusion peptide (MP-1184) as indicated (10 μg of DP in each dose). On day 35, in vivo CTL activity was measured in three mice per group. Results show mean±SD percent specific killing of cells pulsed with target peptide.

FIG. 17 shows efficacy in the remaining 10 mice per group from FIG. 16 that were challenged by exposure to PfPb-infected mosquitoes, and parasite burden in the liver 40 hours later was measured by qPCR. Results are shown as described in the legend to FIG. 11.

FIG. 18 shows antibody responses elicited by malaria Pam3Cys.T1B microparticles in C57BL/6 mice. Mice were immunized on days 0 and 21 and bled on day 28; sera were tested in ELISA against T1B peptide. Results show the mean±SD anti-T1B IgG antibody titer of 10 mice per group. §P<0.05 compared to the MP-1167 group.

FIG. 19 shows the isotype distribution of the antibody response in the sera from FIG. 18. The T1B ELISA was repeated with a 1:250 dilution of individual sera, and each serum was probed with isotype-specific detection antibodies. Results show the mean±SD of 10 mice per group.

FIG. 20 shows efficacy in mice depicted in FIG. 18. C57BL/6 mice were immunized on days 0, 21, and 42 with Pam3Cys.T1B microparticles and challenged on day 56 by exposure to PfPb-infected mosquitoes. Parasite burden in the liver 40 hours post-challenge was measured by qPCR.

The above-described and other features will be appreciated and understood by those skilled in the art from the following detailed description, drawings, and appended claims.

DETAILED DESCRIPTION

Disclosed herein are multilayer films comprising polypeptide epitopes from a *Plasmodium* protozoan, wherein the multilayer films are capable of eliciting an immune response in a host upon administration to the host. Specifically, the films comprise one or more *Plasmodium falciparum* circumsporozoite protein antigens, wherein the circumsporozoite protein antigens include a T1 epitope, a B epitope and/or a T* epitope. Also included are compositions comprising two or more different multilayer films.

As used herein, the *Plasmodium falciparum* circumsporozoite protein antigens are:

```
T1:
                                   (SEQ ID NO: 1)
DPNANPNVDPNANPNV

B:
                                   (SEQ ID NO: 2)
NANP

T*:
                                   (SEQ ID NO: 3)
EYLNKIQNSLSTEWSPCSVT
```

In certain embodiments, the T1, B or T* epitope, particularly the B epitope, is repeated 2 or more times.

Specifically, the multilayer films comprise alternating layers of oppositely charged polyelectrolytes. Optionally, one or more of the polyelectrolytes is a polypeptide. In certain embodiments, the multilayer films comprise multiple epitopes from a *Plasmodium* protozoan. For example, first and second *Plasmodium* protozoan polypeptide epitopes can be attached to the same or different polyelectrolytes, and/or can be present in the same or different multilayer film. In one embodiment, first and second *Plasmodium* protozoan polypeptide epitopes are covalently attached to the same polyelectrolyte and thus are in the same multilayer film. In another embodiment, first and second *Plasmodium* protozoan polypeptide epitopes are covalently attached to different polyelectrolytes, but are layered within the same multilayer film. In yet another embodiment, first and second *Plasmodium* protozoan polypeptide epitopes are covalently attached to different polyelectrolytes, but are layered in different multilayer films which are subsequently mixed prior to administration.

In one embodiment, a composition comprises a first multilayer film comprising a plurality of oppositely charged polyelectrolyte layers, wherein one of the polyelectrolyte layers in the multilayer film comprises a first antigenic polyelectrolyte, wherein the first antigenic polyelectrolyte comprises a *Plasmodium falciparum* circumsporozoite T1, B or T* epitope covalently linked to a first polyelectrolyte, and wherein the polyelectrolytes in the multilayer film comprise a polycationic material or a polyanionic material having a molecular weight of greater than 1,000 and at least 5 charges per molecule.

The first antigenic polyelectrolyte comprises at least one of a *Plasmodium falciparum* circumsporozoite T1, B or T* epitope. In one embodiment, the first antigenic polyelectrolyte comprises two of the *Plasmodium falciparum* circumsporozoite T1, B and T* epitopes, such as T1T*, T1B or BT*, in any order. In yet another embodiment, the first antigenic polyelectrolyte comprises all three of the *Plasmodium falciparum* circumsporozoite T1, B and T* epitopes.

In one embodiment, the first polyelectrolyte is a polypeptide comprising at least one of a *Plasmodium falciparum* circumsporozoite T1, B or T* epitope. In one embodiment, the first antigenic polypeptide comprises two of the *Plasmodium falciparum* circumsporozoite T1, B and T* epitopes, such as T1T*, T1B or BT*, in any order. The epitopes can be contiguous on the polypeptide chain, or spaced by a spacer region. Similarly, the epitopes can be at the N-terminus of the polypeptide, the C-terminus of the polypeptide, or anywhere in between. In yet another embodiment, the first polyelectrolyte is a polypeptide comprising all three of the *Plasmodium falciparum* circumsporozoite T1, B and T* epitope. The T1, B and T* epitopes can be in a contiguous part of the polypeptide, or any or all of the epitopes can be separated by a spacer region.

It is noted that when the first antigenic polyelectrolye is a polypeptide, the polypeptide contains sufficient charge for deposition into a polypeptide multilayer film. In one embodiment, the net charge per residue of the polypeptide is greater than or equal to 0.1, 0.2, 0.3, 0.4 or 0.5 at pH 7.0, as explained herein.

In another embodiment, instead of the *Plasmodium falciparum* circumsporozoite T1, B and T* epitopes being on the same polyelectrolytes, two or three epitopes can be presented on separate polyelectrolytes, and layered into the same multilayer film. In one embodiment, the first multilayer film further comprises a second antigenic polyelectrolyte comprising a *Plasmodium falciparum* circumsporozoite T1, B or T* epitope covalently linked to a second polyelectrolyte, wherein the first and second antigenic polyelectrolytes comprise different *Plasmodium falciparum* circumsporozoite epitopes. In a further embodiment, the first multilayer film further comprises a third antigenic polyelectrolyte comprising a *Plasmodium falciparum* circumsporozoite T1, B or T* epitope covalently linked to a third polyelectrolyte, wherein the first, second and third antigenic polyelectrolytes comprise different *Plasmodium falciparum* circumsporozoite epitopes. In one embodiment, the first, second and/or third polyelectrolyte is a polypeptide.

In one embodiment, a first, second and optionally third polyelectrolyte is presented in a separate multilayer film, such as two or three individual populations of coated cores, each population comprising a different multilayer film. Thus, in one embodiment, a composition comprises a first multilayer film as described above and a second multilayer film comprising a plurality of oppositely charged polyelectrolyte layers, wherein one of the layers in the second multilayer film comprises a second antigenic polyelectrolyte, wherein the second antigenic polyelectrolyte comprises a *Plasmodium falciparum* circumsporozoite T1, B or T* epitope covalently linked to a second polyelectrolyte, wherein the first and second antigenic polyelectrolytes comprise different *Plasmodium falciparum* circumsporozoite epitopes. In a further embodiment, the composition further comprises a third multilayer film comprising a plurality of oppositely charged polyelectrolyte layers, wherein one of the layers in the third multilayer film comprises a third antigenic polyelectrolyte, wherein the third antigenic polyelectrolyte comprises a *Plasmodium falciparum* circumsporozoite T1, B or T* epitope covalently linked to a third polyelectrolyte, wherein the first, second and third antigenic polyelectrolytes comprise different *Plasmodium falciparum* circumsporozoite epitopes. In certain embodiments, the first, second and or third polyelectrolyte is a polypeptide. In some embodiments, the first, second and third multilayer films are layered onto core particles, such that a composition comprises two or three distinct populations of particles.

In certain embodiments, the multilayer films further comprise a toll-like receptor ligand. As used herein, toll-like receptor ligands, or TLR ligands, are molecules that bind to TLRs and either activate or repress TLR receptors. Activation of TLR signaling through recognition of pathogen-associated molecular patterns (PAMPs) and mimics leads to the transcriptional activation of genes encoding pro-inflammatory cytokines, chemokines and co-stimulatory molecules, which can control the activation of the antigen-specific adaptive immune response. TLRs have been pursued as potential therapeutic targets for various inflammatory diseases and cancer. Following activation, TLRs induce the expression of a number of protein families, including inflammatory cytokines, type I interferons, and chemokines. TLR receptor ligands can function as adjuvants for the immune response.

Exemplary TLR ligands include a TLR1 ligand, a TLR2 ligand, a TLR3 ligand, a TLR4 ligand, a TLR5 ligand, a TLR6 ligand, a TLR 7 ligand, a TLR8 ligand, a TLR9 ligand and combinations thereof.

Exemplary TLR1 ligands include bacterial lipopeptide. Exemplary TLR2 ligands include lipopeptides such as Pam3Cys ([N-palmitoyl-S-[2,3-bis(palmitoyloxy)propyl] cysteine]) and Pam2Cys ($Pam_2Cys$ [S-[2,3-bis(palmitoyloxy)propyl]cysteine]). Exemplary TLR6 ligands are diacyl lipopeptides. TLR1 and TLR6 require heterodimerization with TLR2 to recognize ligands. TLR1/2 are activated by triacyl lipoprotein (or a lipopeptide, such as Pam3Cys), whereas TLR6/2 are activated by diacyl lipoproteins (e.g., Pam2Cys), although there may be some cross-recognition.

An exemplary TLR3 ligand is Poly(I:C). Exemplary TLR4 ligands are lipopolysaccharide (LPS) and monophospholipid A (MPL). An exemplary TLR5 ligand is flagellin. An exemplary TLR7 ligand is imiquimod. An exemplary TLR8 ligand is single-stranded RNA. An exemplary TLR9 ligand is unmethylated CpG Oligodeoxynucleotide DNA.

In one embodiment, the first, second or third antigenic polyelectrolyte, e.g., an antigenic polypeptide, has a TLR ligand covalently attached thereto. For example, Pam3Cys can be covalently coupled to a polypeptide chain by standard polypeptide synthesis chemistry.

In another embodiment, a substrate such as a template core has deposited thereon a TLR ligand prior to deposition of polyelectrolyte layers. In another embodiment, a TLR ligand is co-deposited with one or more polyelectrolyte layers during assembly of the multilayer film.

In one embodiment, the multilayer film is deposited on a core particle, such as a $CaCO_3$ nanoparticle, a latex particle, or an iron particle. Particle sizes on the order of 5 nanometers (nm) to 500 micrometers (nm) in diameter are particularly useful, as are larger particles having diameters of 1 μm or more, such as 3 μm diameter particles. Particles made of other materials can also be used as cores provided that they are biocompatible, have controllable size distribution, and have sufficient surface charge (either positive or negative) to bind polyelectrolyte peptides. Examples include nanoparticles and microparticles made of materials such as polylactic acid (PLA), polylactic acid glycolic acid copolymer (PLGA), polyethylene glycol (PEG), chitosan, hyaluronic acid, gelatin, or combinations thereof. Core particles could also be made of materials that are believed to be inappropriate for human use provided that they can be dissolved and separated from the multilayer film following film fabrication. Examples of the template core substances include organic polymers such as latex or inorganic materials such as silica.

Polyelectrolyte multilayer films are thin films (e.g., a few nanometers to micrometers thick) composed of alternating layers of oppositely charged polyelectrolytes. Such films can be formed by layer-by-layer assembly on a suitable substrate. In electrostatic layer-by-layer self-assembly ("LBL"), the physical basis of association of polyelectrolytes is electrostatic attraction. Film buildup is possible because the sign of the surface charge density of the film reverses on deposition of successive layers. The generality and relative simplicity of the LBL film process permits the deposition of many different types of polyelectrolyte onto many different types of surface. Polypeptide multilayer films are a subset of polyelectrolyte multilayer films, comprising at least one layer comprising a charged polypeptide, herein referred to as a designed polypeptide. A key advantage of polypeptide multilayer films over films made from other polymers is their biocompatibility. LBL films can also be used for encapsulation. Applications of polypeptide films and microcapsules include, for example, nano-reactors, biosensors, artificial cells, and drug delivery vehicles.

The term "polyelectrolyte" includes polycationic and polyanionic materials having a molecular weight of greater than 1,000 and at least 5 charges per molecule. Suitable polycationic materials include, for example, polypeptides and polyamines. Polyamines include, for example, a polypeptide such as poly-L-lysine (PLL) or poly-L-ornithine, polyvinyl amine, poly(aminostyrene), poly(aminoacrylate), poly (N-methyl aminoacrylate), poly (N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), poly (diallyl dimethylammonium chloride), poly(N,N,N-trimethylaminoacrylate chloride), poly(methyacrylamidopropyltrimethyl ammonium chloride), chitosan and combinations comprising one or more of the foregoing polycationic materials. Suitable polyanionic materials include, for example, a polypeptide such as poly-L-glutamic acid (PGA) and poly-L-aspartic acid, a nucleic acid such as DNA and RNA, alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose, acidic polysaccharides, and croscarmelose, synthetic polymers and copolymers containing pendant carboxyl groups, and combinations comprising one or more of the foregoing polyanionic materials. In one embodiment, the *Plasmodium* protozoan epitope and the polyelectrolyte have the same sign of charge.

In one embodiment, one or more polyelectrolyte layers of the film, optionally including the polyelectrolyte comprising the *Plasmodium* protozoan epitope, is a designed polypeptide. In one embodiment, the design principles for polypeptides suitable for electrostatic layer-by-layer deposition are elucidated in U.S. Patent Publication No. 2005/0069950 now U.S. Pat. No. 7,348,399 issued Mar. 25, 2008, incorporated herein by reference for its teaching of polypeptide multilayer films. Briefly, the primary design concerns are the length and charge of the polypeptide. Electrostatics is the most important design concern because it is the basis of LBL. Without suitable charge properties, a polypeptide may not be substantially soluble in aqueous solution at pH 4 to 10 and cannot readily be used for the fabrication of a multilayer film by LBL. Other design concerns include the physical structure of the polypeptides, the physical stability of the films formed from the polypeptides, and the biocompatibility and bioactivity of the films and the constituent polypeptides.

A designed polypeptide means a polypeptide that has sufficient charge for stable binding to an oppositely charged surface, that is, a polypeptide that can be deposited into a layer of a multilayer film wherein the driving force for film formation is electrostatics. A short stable film is a film that once formed, retains more than half its components after incubation at in PBS at 37° C. for 24 hours. In specific embodiments, a designed polypeptide is at least 15 amino acids in length and the magnitude of the net charge per residue of the polypeptide is greater than or equal to 0.1, 0.2, 0.3, 0.4 or 0.5 at pH 7.0. Positively-charged (basic) naturally-occurring amino acids at pH 7.0 are arginine (Arg), histidine (His), ornithine (Orn), and lysine (Lys). Negatively-charged (acidic) naturally-occurring amino acid residues at pH 7.0 are glutamic acid (Glu) and aspartic acid (Asp). A mixture of amino acid residues of opposite charge can be employed so long as the overall net ratio of charge meets the specified criteria. In one embodiment, a designed polypeptide is not a homopolymer. In another embodiment, a designed polypeptide is unbranched.

One design concern is control of the stability of polypeptide LBL films. Ionic bonds, hydrogen bonds, van der Waals interactions, and hydrophobic interactions contribute to the stability of multilayer films. In addition, covalent disulfide bonds formed between sulfhydryl-containing amino acids in the polypeptides within the same layer or in adjacent layers can increase structural strength. Sulfhydryl-containing amino acids include cysteine and homocysteine and these residues can be readily incorporated into synthetic designed peptides. In addition sulfhydryl groups can be incorporated into polyelectrolyte homopolymers such as poly-L-lysine or poly-L-glutamic acid by methods well described in the literature. Sulfhydryl-containing amino acids can be used to "lock" (bond together) and "unlock" layers of a multilayer polypeptide film by a change in oxidation potential. Also, the incorporation of a sulfhydryl-containing amino acid in a designed polypeptide enables the use of relatively short peptides in thin film fabrication, by virtue of intermolecular disulfide bond formation.

In one embodiment, the designed sulfhydryl-containing polypeptides, whether synthesized chemically or produced in a host organism, are assembled by LBL in the presence of a reducing agent to prevent premature disulfide bond formation. Following film assembly, the reducing agent is removed and an oxidizing agent is added. In the presence of the oxidizing agent disulfide bonds form between sufthydryl groups, thereby "locking" together the polypeptides within layers and between layers where thiol groups are present. Suitable reducing agents include dithiothreitol (DTT), 2-mercaptoethanol (BME), reduced glutathione, tris(2-carboxyethyl)phosphine hydrochloride (TCEP), and combinations of more than one of these chemicals. Suitable oxidizing agents include oxidized glutathione, tert-butylhydroperoxide (t-BHP), thimerosal, diamide, 5,5'-dithio-bis-(2-nitrobenzoic acid) (DTNB), 4,4'-dithiodipyridine, sodium bromate, hydrogen peroxide, sodium tetrathionate, porphyrindin, sodium orthoiodosobenzoate, and combinations of more than one of these chemicals.

As an alternative to disulfide bonds, chemistries that produce other covalent bonds can be used to stabilize LBL films. For films comprised of polypeptides, chemistries that produce amide bonds are particularly useful. In the presence of appropriate coupling reagents, acidic amino acids (those with side chains containing carboxylic acid groups such as aspartic acid and glutamic acid) will react with amino acids whose side chains contain amine groups (such as lysine and ornithine) to form amide bonds. Amide bonds are more stable than disulfide bonds under biological conditions and amide bonds will not undergo exchange reactions. Many reagents can be used to activate polypeptide side chains for amide bonding. Carbodiimide reagents, such as the water soluble 1-ethyl-3-(3-dimethylaminopropyl) carbodiimide (EDC) will react with aspartic acid or glutamic acid at slightly acidic pH, forming an intermediate product that will react irreversibly with an amine to produce an amide bond. Additives such as N-hydroxysuccinimide are often added to the reaction to accelerate the rate and efficiency of amide formation. After the reaction the soluble reagents are removed from the nanoparticles or microparticles by centrifugation and aspiration. Examples of other coupling reagents include diisopropylcarbodiimide, HBTU, HATU, HCTU, TBTU, and PyBOP. Examples of other additives include sulfo-N-hydroxysuccinimide, 1-hydroxbenzotriazole, and 1-hydroxy-7-aza-benzotriazole. The extent of amide cross linking can be controlled by modulating the stoichiometry of the coupling reagents, the time of reaction, or the temperature of the reaction, and can be monitored by techniques such as Fourier transform-infrared spectroscopy (FT-IR).

Covalently cross-linked LBL films have desirable properties such as increased stability. Greater stability allows for more stringent conditions to be used during nanoparticle, microparticle, nanocapsule, or microcapsule fabrication. Examples of stringent conditions include high temperatures, low temperatures, cryogenic temperatures, high centrifugation speeds, high salt buffers, high pH buffers, low pH buffers, filtration, and long term storage.

A method of making a polyelectrolyte multilayer film comprises depositing a plurality of layers of oppositely charged chemical species on a substrate. In one embodiment, at least one layer comprises a designed polypeptide. Successively deposited polyelectrolytes will have opposite net charges. In one embodiment, deposition of a polyelectrolyte comprises exposing the substrate to an aqueous solution comprising a polyelectrolyte at a pH at which it has a suitable net charge for LBL. In other embodiments, the deposition of a polyelectrolyte on the substrate is achieved by sequential spraying of solutions of oppositely charged polypeptides. In yet other embodiments, deposition on the substrate is by simultaneous spraying of solutions of oppositely charged polyelectrolytes.

In the LBL method of forming a multilayer film, the opposing charges of the adjacent layers provide the driving force for assembly. It is not critical that polyelectrolytes in opposing layers have the same net linear charge density, only that opposing layers have opposite charges. One standard film assembly procedure by deposition includes forming aqueous solutions of the polyions at a pH at which they are ionized (i.e., pH 4-10), providing a substrate bearing a surface charge, and alternating immersion of the substrate into the charged polyelectrolyte solutions. The substrate is optionally washed in between deposition of alternating layers.

The concentration of polyelectrolyte suitable for deposition of the polyelectrolyte can readily be determined by one of ordinary skill in the art. An exemplary concentration is 0.1 to 10 mg/mL. For typical non-polypeptide polyelectrolytes such as poly(acrylic acid) and poly(allylamine hydrochloride), typical layer thicknesses are about 3 to about 5 Å, depending on the ionic strength of solution. Short polyelectrolytes typically form thinner layers than long polyelectrolytes. Regarding film thickness, polyelectrolyte film thickness depends on humidity as well as the number of layers and composition of the film. For example, PLL/PGA films 50 nm thick shrink to 1.6 nm upon drying with nitrogen. In general, films of 1 nm to 100 nm or more in thickness can be formed depending on the hydration state of the film and the molecular weight of the polyelectrolytes employed in the assembly.

In addition, the number of layers required to form a stable polyelectrolyte multilayer film will depend on the polyelectrolytes in the film. For films comprising only low molecular weight polypeptide layers, a film will typically have 4 or more bilayers of oppositely charged polypeptides. For films comprising high molecular weight polyelectrolytes such as poly(acrylic acid) and poly(allylamine hydrochloride), films comprising a single bilayer of oppositely charged polyelectrolyte can be stable. Studies have shown that polyelectrolyte films are dynamic. The polyelectrolytes contained within a film can migrate between layers and can exchange with soluble polyelectrolytes of like charge when suspended in a polyelectrolyte solution. Moreover polyelectrolyte films can disassemble or dissolve in response to a change in environment such as temperature, pH, ionic strength, or oxidation potential of the suspension buffer. Thus some polyelectrolytes and particularly peptide polyelectrolytes exhibit transient stability. The stability of peptide polyelectrolyte films can be monitored by suspending the films in a suitable buffer under controlled conditions for a fixed period of time, and then measuring the amounts of the peptides within the film with a suitable assay such as amino acid analysis, HPLC assay, or fluorescence assay. Peptide polyelectrolyte films are most stable under conditions that are relevant to their storage and usage as vaccines, for example in neutral buffers and at ambient temperatures such as 4° C. to 37° C. Under these conditions stable peptide polyelectrolyte films will retain most of their component peptides for at least 24 hours and often up to 14 days and beyond.

In one embodiment, a designed polypeptide comprises one or more surface adsorption regions covalently linked to one or more *Plasmodium* protozoan epitopes, wherein the designed polypeptide and the one or more surface adsorption regions have the same sign of charge, that is, are both positively or both negatively charged overall. As used herein, a surface adsorption region is a charged region of a designed polypeptide that advantageously provides sufficient charge so that a peptide containing an epitope from a *Plasmodium* protozoan, for example, can be deposited into a multilayer film. In one embodiment, the one or more surface adsorption regions and the one or more *Plasmodium* protozoan epitopes have the same net polarity. In another embodiment, the solubility of the designed polypeptide at pH 4 to 10 is greater than or equal to about 0.1 mg/mL. In another embodiment, the solubility of the designed polypeptide at pH 4 to 10 is greater than or equal to about 1 mg/mL. The solubility is a practical limitation to facilitate deposition of the polypeptides from aqueous solution. A practical upper limit on the degree of polymerization of an antigenic polypeptide is about 1,000 residues. It is conceivable, however, that longer composite polypeptides could be realized by an appropriate method of synthesis.

In one embodiment, a designed polypeptide comprises a single antigenic *Plasmodium* protozoan epitope flanked by two surface adsorption regions, an N-terminal surface adsorption region and a C-terminal surface adsorption region. In another embodiment, a designed polypeptide comprises a single antigenic *Plasmodium* protozoan epitope flanked by one surface adsorption region linked to the N-terminus of the *Plasmodium* protozoan epitope. In another embodiment, a designed polypeptide comprises a single antigenic *Plasmodium* protozoan epitope flanked by one surface adsorption regions linked to the C-terminus of the *Plasmodium* protozoan epitope.

Each of the independent regions (e.g., *Plasmodium* protozoan epitopes and surface adsorption regions) of the designed polypeptide can be synthesized separately by solution phase peptide synthesis, solid phase peptide synthesis, or genetic engineering of a suitable host organism. Solution phase peptide synthesis is the method used for production of most of the approved peptide pharmaceuticals on the market today. A combination of solution phase and solid phase methods can be used to synthesize relatively long peptides and even small proteins. Peptide synthesis companies have the expertise and experience to synthesize difficult peptides on a fee-for-service basis. The syntheses are performed under good manufacturing practices (GMP) conditions and at a scale suitable for clinical trials and commercial drug launch.

Alternatively, the various independent regions can be synthesized together as a single polypeptide chain by solution-phase peptide synthesis, solid phase peptide synthesis or genetic engineering of a suitable host organism. The choice of approach in any particular case will be a matter of convenience or economics.

If the various *Plasmodium* protozoan epitopes and surface adsorption regions are synthesized separately, once purified, for example, by ion exchange chromatography or by high performance liquid chromatography, they are joined by peptide bond synthesis. That is, the N-terminus of the surface adsorption region and the C-terminus of the *Plasmodium* protozoan epitope are covalently joined to produce the designed polypeptide. Alternatively, the C-terminus of the surface adsorption region and the N-terminus of the *Plasmodium* protozoan epitope are covalently joined to produce the designed polypeptide. The individual fragments can be synthesized by solid phase methods and obtained as fully protected, fully unprotected, or partially protected segments. The segments can be covalently joined in a solution phase reaction or solid phase reaction. If one polypeptide fragment contains a cysteine as its N-terminal residue and the other polypeptide fragment contains a thioester or a thioester precursor at its C-terminal residue the two fragments will couple spontaneously in solution by a specific reaction commonly known (to those skilled in the art) as Native Ligation. Native Ligation is a particularly attractive option for designed peptide synthesis because it can be performed with fully deprotected or partially protected peptide fragments in aqueous solution and at dilute concentrations.

In one embodiment, the *Plasmodium* protozoan epitopes and/or surface adsorption regions are joined by peptidic or non-peptidic linkages as described in U.S. Pat. No. 7,723,294, incorporated herein by reference for its teaching of the use of non-peptidic linkages to join segments of polypeptides for use in multilayer films. Suitable non-peptidic linkers include, for example, alkyl linkers such as $—NH—(CH_2)_s—C(O)—$, wherein s=2-20. Alkyl linkers are optionally substituted by a non-sterically hindering group such as lower alkyl (e.g., $C_1$-$C_6$), lower acyl, halogen (e.g., Cl, Br), CN, $NH_2$, phenyl, and the like. Another exemplary non-peptidic linker is a polyethylene glycol linker such as $—NH—(CH_2—CH_2—O)_n$, —C(O)— wherein n is such that the linker has a molecular weight of 100 to 5000 Da, specifically 100 to 500 Da. Many of the linkers described herein are available from commercial vendors in a form suitable for use in solid phase peptide synthesis.

In one embodiment, one or more of the polypeptide epitopes from a *Plasmodium* protozoan is covalently attached to one or more of the polyelectrolyes, such as a polypeptide or other polyelectrolyte, through covalent bonds. Examples of suitable covalent bonds include amides, esters, ethers, thioethers, and disulfides. One skilled in the art can take advantage of a range of functional groups found within the epitope peptide to engineer a bond to a suitable electrolyte. For instance, a carboxylic acid in the epitope peptide can be found either at the C-terminal or on the side chain of amino acids aspartic acid or glutamic acid. Carboxylic acids can be activated with suitable peptide coupling reagents such as 1-ethyl-3-(3-dimethylaminopropyl) carbodiimide (EDC) for reaction with primary or secondary amines that are found in peptide polyelectrolytes such as poly-L-lysine. The resulting amide bond is stable under ambient conditions. Conversely, the acid groups in a peptide polyelectrolyte can be activated with EDC for reaction with amine groups in the epitope peptide. Useful amine groups can be found at the epitope peptide's N-terminal or on the side chain of lysine residues.

Epitope peptides can also be attached to polyelectrolytes via disulfide bonds. Polyelectrolytes such as PGA or PLL can be chemically modified so that a fraction of their side chains contain sulfhydryl groups. In the presence of a suitable oxidant, those sulfydryls will react with the sulfhydryl group of a cysteine residue contained within the epitope peptide. The cysteine can either be a native cysteine from the protein sequence of a pathogen such as a *Plasmodium* protozoan or it can be a non-native cysteine that was intentionally incorporated into the epitope during peptide synthesis. Suitable oxidants include DTNB, 2,2'-dithiopyridine, hydrogen peroxide, cystine, and oxidized glutathione. The attachment of epitope peptides to polyelectrolytes via disulfide bonds is particularly useful. The disulfides are stable under normal conditions of film fabrication and storage but are readily cleaved by reducing agents found naturally in cells, which frees up the epitope peptide for immune processing.

Epitope peptides can also be attached to polyelectrolytes via thioether bonds. Synthetic epitope peptides can be synthesized with appropriate electrophiles such as haloacetyl groups which react specifically with sulfhydryls. For instance, an epitope peptide containing a chloroacetyl at its N-terminal will form a stable bond to sulfhydryl bearing polyelectrolytes such as PGA-SH described above.

Epitope peptides can also be attached covalently to polyelectrolytes through bifunctional linker molecules. Bifunctional linkers usually contain two electrophilic groups that can react with nucleophiles present on either the epitope peptide or the polyelectrolyte molecule. Two classes of linker molecules are sold commercially, homobifunctional linkers and heterobifunctional linkers. Homobifunctional linkers contain two copies of an electrophilic group joined by a nonreactive spacer. Often the electophiles are active esters, such as N-hydroxysuccinimide (NHS) esters or sulfo-N-hyrdoxysuccinimide esters (sulfo NHS) which react with nucleophilic amines. Examples of homobifunctional NHS esters include bis(sulfosuccinimidyl) suberate, disuccinimidyl glutarate, dithiobis(succinimidyl) propionate, disuccinimidyl suberate, disuccinimidyl tartrate. Sometimes the electophiles are aldehyde groups that form imides with nucleophilic amines on the epitope and polyelectrolyte molecules. The imide bonds are transiently stable but can be converted to stable structures with reducing agents such as sodium borohydride or catalytic hydrogenation. The most commonly used homobifunctional aldehyde linker is glutaraldehyde.

Other commonly used homobifunctional linkers contain electrophiles that react specifically with nucleophilic thiols, which can be used to link cysteine containing epitope peptides to sulfhydryl containing polyelectrolytes as described above. Examples of sulfhydryl specific homobifunctional linkers include 1,4-bismaleimidobutane, 1,4 bismaleimidyl-2,3-dihydroxybutane, vbismaleimidohexane, bis-maleimidoethane, 1,4-di-[3'-(2'-pyridyldithio)-propionamido]butane, dithio-bismaleimidoethane, 1,6-hexane-bis-vinylsulfone.

Members of the heterobifunctional class of cross linking reagents contain two different reactivity groups, often but not always electrophiles, which react specifically with different functional groups in substrate molecules. Particularly useful are linkers that contain one electrophilic group that is specific for a sulfhydryl and another electrophile that is specific for an amine. Examples of these reagents include N-sulfosuccinimidyl[4-iodoacetyl]aminobenzoate, N-succinimidyl[4-iodoacetyl]aminobenzoate, succinimidyl 3-[bromoacetamido]propionate, N-succinimidyl iodoacetate, sulfosuccinimidyl 4-[N-maleimidomethyl]cyclohexane-1-carboxylate, succinimidyl 4-[N-maleimidomethyl]cyclohexane-1-carboxylate, ([N-e-maleimidocaproyloxy]sulfosuccinimide ester, m-maleimidobenzoyl-N-hydroxysulfosuccinimide ester, N-succinimidyl 3-(2-pyridyldithio)-propionate, succinimidyl 6-(3-[2-pyridyldithio]-propionamido)hexanoate, 4-succinimidyloxycarbonyl-methyl-a-[2-pyridyldithio]toluene.

The wide range of functionality that is normally present in both epitope peptides and polyelectrolytes or which can easily be installed in either molecule allows one to choose a linking strategy that best fits the substrates of interest. A likely example is the linking of a cysteine containing epitope peptide to PLL.

The polypeptide segments can be joined in a variety of ways, depending upon the chemistry of the non-peptidic linker. For example, the N-terminus of the first polypeptide segment is joined to the C-terminus of the second polypeptide segment; the N-terminus of the first polypeptide segment is joined to the N-terminus of the second polypeptide segment; the C-terminus of the first polypeptide segment is joined to the C-terminus of the second polypeptide segment; the C-terminus of the first polypeptide segment is joined to the N-terminus of the second polypeptide segment; the C-terminus or the N-terminus of the first polypeptide segment is joined to a pendant side chain of the second polypeptide segment; or the C-terminus or the N-terminus of the second polypeptide segment is joined to a pendant side chain of the first polypeptide segment. Regardless of the point of attachment, however, the first and second segments are covalently joined by a non-peptidic linker.

In one embodiment, a designed polypeptide is a unique combination of covalently attached one or more surface adsorption region(s) and one or more *Plasmodium* protozoan epitope(s). There is no particular limitation on the length of the *Plasmodium* protozoan epitopes, which can be linear epitopes or conformational epitopes. Epitopes can comprise anywhere from about three amino acid resides up to several hundred amino acid residues for complex conformational epitopes.

In one embodiment, a designed polypeptide comprises one *Plasmodium* protozoan epitope and one surface adsorption region. In another embodiment, a designed polypeptide comprises one *Plasmodium* protozoan epitope and two surface adsorption regions, one attached to the N-terminus of the *Plasmodium* protozoan epitope and one attached to the C-terminus of the *Plasmodium* protozoan epitope. The purpose of the surface adsorption region(s) is to enable adsorption of the polypeptide onto an oppositely charged surface in order to build a multilayer film.

The number of surface adsorption regions in a designed polypeptide relative to the number and/or length of the *Plasmodium* protozoan epitopes is related to the solubility requirement. For example, if the *Plasmodium* protozoan epitope is a short amino acid sequence of, for example, three amino acid residues, only one surface adsorption region of at least eight amino acid residues will be required to adsorb the designed polypeptide onto a suitably charged surface. If, by contrast, the *Plasmodium* protozoan epitope is a soluble folded structural domain of a protein comprising, for example, 120 amino acid residues, two surface adsorption regions may be required to impart enough charge for the designed polypeptide to be water soluble and suitable for adsorption. The surface adsorption regions could be contiguous and located at the N-terminus of the domain, contiguous and located at the C-terminus of the domain, or noncontiguous with one at the N-terminus and one at the C-terminus. Additionally, a *Plasmodium* protozoan epitope may contain a charged segment (either negatively charged or positively charged) within its native sequence that can serve as a surface adsorption region.

A polypeptide or antigen may contain one or more distinct antigenic determinants. An antigenic determinant may refer to an immunogenic portion of a multichain protein.

Methods and techniques for determining the location and composition of an antigenic determinant or epitope for a specific antibody are well known in the art. These techniques can be used to identify and/or characterize epitopes for use as *Plasmodium* protozoan epitopes. In one embodiment, mapping/characterization methods of an epitope for an antigen specific antibody can be determined by epitope "footprinting" using chemical modification of the exposed amines/carboxyls in the antigenic protein. One example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions may be identified at this point by peptic proteolysis, fast microbore high-performance liquid chromatography separation, and/or electrospray ionization mass spectrometry.

In another embodiment, a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with $^{15}N$ so that only signals corresponding to the antigen and no signals from the antigen binding peptide are seen in the NMR spectrum. Antigen signals originating from amino acids involved in the interaction with the antigen binding peptide typically will shift position in the spectra of the complex compared to the spectra of the free antigen, and the amino acids involved in the binding may be identified that way.

In another embodiment, epitope mapping/characterization may be done by peptide scanning. In this approach, a series of overlapping peptides spanning the full length of the polypeptide chain of an antigen are prepared and tested individually with regard to immunogenicity. The antibody titer of the corresponding peptide antigen is determined by a standard method, e.g., enzyme-linked immunosorbent assay. The various peptides can then be ranked with regard to immunogenicity, providing an empirical basis for selection of peptide design for vaccine development.

In another embodiment, protease digestion techniques may also be useful in the context of epitope mapping and identification. Antigenic determinant-relevant regions/sequences may be determined by protease digestion, e.g. by using trypsin in a ratio of about 1:50 to antigenic protein overnight (O/N) digestion at 37° C. and pH 7-8, followed by mass spectrometry (MS) analysis for peptide identification. The peptides protected from trypsin cleavage by the antigenic protein may subsequently be identified by comparison of samples subjected to trypsin digestion and samples incubated with CD38BP and then subjected to digestion by e.g. trypsin (thereby revealing a foot print for the binder). Other enzymes like chymotrypsin, pepsin, etc., may also or alternatively be used in a similar epitope characterization method. Moreover, protease digestion can provide a quick method for determining the location of a potential antigenic determinant sequence within a known antigenic protein using a known antibody. In another embodiment, protease digestion techniques may also be useful in the context of epitope mapping and identification.

Further disclosed herein is an immunogenic composition, said immunogenic composition comprising a multilayer film comprising two or more layers of polyelectrolytes, wherein adjacent layers comprise oppositely charged polyelectrolytes, wherein one layer comprises a *Plasmodium* protozoan epitope. The immunogenic composition optionally further comprises one or more layers comprising a designed polypeptide.

In one embodiment, an immunogenic composition comprises a plurality of *Plasmodium* protozoan epitopes, either on the same or different polyelectrolytes, for example, designed polypeptides. The plurality of antigenic determinants may be from the same or different infectious agents. In one embodiment, the immunogenic composition comprises a plurality of unique antigenic polyelectrolytes. In another embodiment, the immunogenic composition comprises a plurality of immunogenic polyelectrolytes comprising multiple *Plasmodium* protozoan epitopes within each polyelectrolyte. An advantage of these immunogenic compositions is that multiple antigenic determinants or multiple conformations of a single linear antigenic determinant can be present in a single synthetic vaccine particle. Such compositions with multiple antigenic determinants can potentially yield antibodies against multiple epitopes, increasing the odds that at least some of the antibodies generated by the immune system of the organism will neutralize the pathogen or target specific antigens on cancer cells, for example.

The immunogenicity of an immunogenic composition may be enhanced in a number of ways. In one embodiment, the multilayer film optionally comprises one or more additional immunogenic bioactive molecules. Although not necessary, the one or more additional immunogenic bioactive molecules will typically comprise one or more additional antigenic determinants. Suitable additional immunogenic bioactive molecules include, for example, a drug, a protein, an oligonucleotide, a nucleic acid, a lipid, a phospholipid, a carbohydrate, a polysaccharide, a lipopolysaccharide, a low molecular weight immune stimulatory molecule, or a combination comprising one or more of the foregoing bioactive molecules. Other types of additional immune enhancers include a functional membrane fragment, a membrane structure, a virus, a pathogen, a cell, an aggregate of cells, an organelle, or a combination comprising one or more of the foregoing bioactive structures.

In one embodiment, the multilayer film optionally comprises one or more additional bioactive molecules. The one or more additional bioactive molecule can be a drug. Alternatively, the immunogenic composition is in the form of a hollow shell or a coating surrounding a core. The core comprises a variety of different encapsulants, for example, one or more additional bioactive molecules, including, for example, a drug. Thus, the immunogenic compositions designed as described herein could also be used for combined therapy, e.g., eliciting an immune response and for targeted drug delivery. Micron-sized "cores" of a suitable therapeutic material in "crystalline" form can be encapsulated by immunogenic composition comprising the antigenic polypeptides, and the resulting microcapsules could be used for drug delivery. The core may be insoluble under some conditions, for instance high pH or low temperature, and soluble under the conditions where controlled release will occur. The surface charge on the crystals can be determined by ζ-potential measurements (used to determine the charge in electrostatic units on colloidal particles in a liquid medium). The rate at which microcapsule contents are released from the interior of the microcapsule to the surrounding environment will depend on a number of factors, including the thickness of the encapsulating shell, the antigenic polypeptides used in the shell, the presence of disulfide bonds, the extent of cross-linking of peptides, temperature, ionic strength, and the method used to assemble the peptides. Generally, the thicker the capsule, the longer the release time.

In another embodiment, the additional immunogenic biomolecule is a nucleic acid sequence capable of directing host organism synthesis of a desired immunogen or interfering with the expression of genetic information from a pathogen. In the former case, such a nucleic acid sequence is, for example, inserted into a suitable expression vector by methods known to those skilled in the art. Expression vectors suitable for producing high efficiency gene transfer in vivo include retroviral, adenoviral and vaccinia viral vectors. Operational elements of such expression vectors include at least one promoter, at least one operator, at least one leader sequence, at least one terminator codon, and any other DNA sequences necessary or preferred for appropriate transcription and subsequent translation of the vector nucleic acid. In particular, it is contemplated that such vectors will contain at least one origin of replication recognized by the host organism along with at least one selectable marker and at least one promoter sequence capable of initiating transcription of the nucleic acid sequence. In the latter case, multiple copies of such a nucleic acid sequence will be prepared for delivery, for example, by encapsulation of the nucleic acids within a polypeptide multilayer film in the form of a capsule for intravenous delivery.

In construction of a recombinant expression vector, it should additionally be noted that multiple copies of the nucleic acid sequence of interest and its attendant operational elements may be inserted into each vector. In such an embodiment, the host organism would produce greater amounts per vector of the desired protein. The number of multiple copies of the nucleic acid sequence which may be inserted into the vector is limited only by the ability of the resultant vector due to its size, to be transferred into and replicated and transcribed in an appropriate host microorganism.

In a further embodiment, the immunogenic composition comprises a mixture of antigenic polyelectrolytes/immunogenic bioactive molecules. These may be derived from the same antigen, they may be different antigens from the same infectious agent or disease, or they may be from different infectious agents or diseases. The complex or mixture will therefore raise an immune response against a number of antigens and possibly a number of infectious agents or diseases as specified by the antigenic peptide/protein components of the delivery system.

In one embodiment, the multilayer film/immunogenic composition evokes a response from the immune system to a pathogen. In one embodiment, a vaccine composition comprises an immunogenic composition in combination with a pharmaceutically acceptable carrier. Thus a method of vaccination against a pathogenic disease comprises the administering to a subject in need of vaccination an effective amount of the immunogenic composition.

Pharmaceutically acceptable carriers include, but are not limited to, large, slowly metabolized macromolecules such as proteins, polysaccharides, polylactic acids, polyglycolic acids, polymeric amino acids, amino acid copolymers, inactive virus particles, and the like. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition can also contain liquids, such as water, saline, glycerol, and ethanol, as well as substances such as wetting agents, emulsifying agents, or pH buffering agents. Liposomes can also be used as carriers.

A method of eliciting an immune response against a disease or pathogen in a vertebrate (e.g., vaccination) comprises administering an immunogenic composition comprising a multilayer film comprising a *Plasmodium* protozoan epitope. In one embodiment, the polyelectrolyte containing the *Plasmodium* protozoan epitope is in the most exterior or solvent-exposed layer of the multilayer film. The immunogenic composition can be administered orally, intranasally, intravenously, intramuscularly, subcutaneously, intraperitoneally, sublingually, intradermally, pulmonary, or transdermally, either with or without a booster dose. Generally, the compositions are administered in a manner compatible with the dosage formulation, and in such amount as will be prophylactically and/or therapeutically effective. Precise amounts of immunogenic composition to be administered depend on the judgment of the practitioner and may be peculiar to each subject. It will be apparent to those of skill in the art that the therapeutically effective amount of an immunogenic composition will depend, inter alia, upon the administration schedule, the unit dose of antigen administered, whether the compositions are administered in combination with other therapeutic agents, and the immune status and health of the recipient. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing.

The immunogenic composition optionally comprises an adjuvant. Adjuvants in general comprise substances that boost the immune response of the host in a non-specific manner. Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

It is contemplated that an immune response may be elicited via presentation of any protein or peptide capable of eliciting such a response. In one embodiment, the antigen is a key epitope, which gives rise to a strong immune response to a particular agent of infectious disease, i.e., an immunodominant epitope. If desired, more than one antigen or epitope may be included in the immunogenic composition in order to increase the likelihood of an immune response.

In one embodiment, multiple *Plasmodium* protozoan peptide or protein epitopes are incorporated into an LBL film. The distinct epitopes can by synthesized or expressed within a single designed peptide molecule. Placing multiple epitopes within a single designed peptide is expected to have certain advantages. For example it should simplify the LBL fabrication process and increase reproducibility. Additionally, placing multiple epitopes within a single designed peptide will lock the molar ratios of the distinct epitopes in a desired ratio, for example 1:1.

Alternatively the epitopes can be incorporated into separate designed peptides. The designed peptides are incorporated into an LBL film during one or more layering steps. Fabrication of films using multiple distinct designed peptides can also present certain advantages. It should simplify designed peptide synthesis reducing costs. It will also enable the relative doses of each designed peptide within the film to be varied and optimized. If, for example, preclinical or clinical biological data indicated that an optimal vaccine should contain five copies of one epitope to every copy of a second epitope (5:1 ratio) the separate epitope designed peptide approach would facilitate the manufacture of such a vaccine.

Designed peptides adsorb to the surface of an LBL films by virtue of the electrostatic attraction between the charged surface adsorption regions(s) of the designed peptide and the oppositely charged surface of the film. The efficiency of adsorption will depend largely upon the composition of the surface adsorption region(s). Thus designed peptides with different epitopes but similar surface adsorption regions(s) will adsorb with similar efficiency. To fabricate a film with two distinct designed peptides each at a 1:1 molar ratio one could mix the peptides at that molar ratio and deposit them simultaneously at a particular layer. Alternatively, one could deposit each peptide individually at separate layers. The molar ratio of peptides adsorbed will largely mirror that relative concentrations at which they were layered or the number of layering steps during which they were incorporated.

The quantity of designed peptides incorporated into an LBL film can be measured in a variety of ways. Quantitative amino acid analysis (AAA) is particularly well suited to this purpose. Films containing designed peptides are decomposed to their constituent amino acids by treatment with concentrated hydrochloric acid (6 M) and heating, typically at 115° C. for 15 hours. The amounts of each amino acid are then measured using chromatographic techniques well known to those skilled in the art. Amino acids that occur in only one of the designed peptides in a film can be used as tracers for that peptide. When designed peptides lack unique amino acids, non-natural amino acids (e.g. aminobutyric acid or homovaline) can be incorporated into designed peptides during synthesis. These tracer amino acids are readily identified during the AAA experiment and can be used to quantitate the amount of peptide in the film.

As used herein, a specific T-cell response is a response that is specific to an epitope of interest, specifically a *Plasmodium* protozoan epitope. A specific T-cell response is an IFNγ and/or an IL-5 T-cell response.

As used herein, a specific antibody response is a response that is specific to an epitope of interest, specifically a *Plasmodium* protozoan epitope as disclosed herein.

As used herein, "layer" means a thickness increment, e.g., on a template for film formation, following an adsorption step. "Multilayer" means multiple (i.e., two or more) thickness increments. A "polyelectrolyte multilayer film" is a film comprising one or more thickness increments of polyelectrolytes. After deposition, the layers of a multilayer film may not remain as discrete layers. In fact, it is possible that there is significant intermingling of species, particularly at the interfaces of the thickness increments. Intermingling, or absence thereof, can be monitored by analytical techniques such as $\zeta$ potential measurements, X-ray photoelectron spectroscopy, and time-of-flight secondary ion mass spectrometry.

"Amino acid" means a building block of a polypeptide. As used herein, "amino acid" includes the 20 common naturally occurring L-amino acids, all other natural amino acids, all non-natural amino acids, and all amino acid mimics, e.g., peptoids.

"Naturally occurring amino acids" means glycine plus the 20 common naturally occurring L-amino acids, that is, alanine, valine, leucine, isoleucine, serine, threonine, cysteine, methionine, aspartic acid, asparagine, glutamic acid, glutamine, arginine, lysine, histidine, phenylalanine, ornithine, tyrosine, tryptophan, and proline.

"Non-natural amino acid" means an amino acid other than any of the 20 common naturally occurring L-amino acids. A non-natural amino acid can have either L- or D-stereochemistry.

"Peptoid," or N-substituted glycine, means an analog of the corresponding amino acid monomer, with the same side chain as the corresponding amino acid but with the side chain appended to the nitrogen atom of the amino group rather than to the $\alpha$-carbons of the residue. Consequently, the chemical linkages between monomers in a polypeptoid are not peptide bonds, which can be useful for limiting proteolytic digestion.

"Amino acid sequence" and "sequence" mean a contiguous length of polypeptide chain that is at least two amino acid residues long.

"Residue" means an amino acid in a polymer or oligomer; it is the residue of the amino acid monomer from which the polymer was formed. Polypeptide synthesis involves dehydration, that is, a single water molecule is "lost" on addition of the amino acid to a polypeptide chain.

As used herein "peptide" and "polypeptide" all refer to a series of amino acids connected one to the other by peptide bonds between the alpha-amino and alpha-carboxy groups of adjacent amino acids, and may contain or be free of modifications such as glycosylation, side chain oxidation, or phosphorylation, provided such modifications, or lack thereof, do not destroy immunogenicity. As used herein, the term "peptide" is meant to refer to both a peptide and a polypeptide or protein.

"Designed polypeptide" means a polypeptide that has sufficient charge for stable binding to an oppositely charged surface, that is, a polypeptide that can be deposited into a layer of a multilayer film wherein the driving force for film formation is electrostatics. In specific embodiments, a designed polypeptide is at least 15 amino acids in length and the magnitude of the net charge per residue of the polypeptide is greater than or equal to 0.1, 0.2, 0.3, 0.4 or 0.5 at pH 7.0. In one embodiment, the ratio of the number of charged residues of the same polarity minus the number of residues of the opposite polarity to the total number of residues in the polypeptide is greater than or equal to 0.5 at pH 7.0. In other words, the magnitude of the net charge per residue of the polypeptide is greater than or equal to 0.5. While there is no absolute upper limit on the length of the polypeptide, in general, designed polypeptides suitable for LBL deposition have a practical upper length limit of 1,000 residues. Designed polypeptides can include sequences found in nature such as *Plasmodium* protozoan epitopes as well as regions that provide functionality to the peptides such as charged regions also referred to herein as surface adsorption regions, which allow the designed polypeptides to be deposited into a polypeptide multilayer film.

"Primary structure" means the contiguous linear sequence of amino acids in a polypeptide chain, and "secondary structure" means the more or less regular types of structure in a polypeptide chain stabilized by non-covalent interactions, usually hydrogen bonds. Examples of secondary structure include $\alpha$-helix, $\beta$-sheet, and $\beta$-turn.

"Polypeptide multilayer film" means a film comprising one or more designed polypeptides as defined above. For example, a polypeptide multilayer film comprises a first layer comprising a designed polypeptide and a second layer comprising a polyelectrolyte having a net charge of opposite polarity to the designed polypeptide. For example, if the first layer has a net positive charge, the second layer has a net negative charge; and if the first layer has a net negative charge, the second layer has a net positive charge. The second layer comprises another designed polypeptide or another polyelectrolyte.

"Substrate" means a solid material with a suitable surface for adsorption of polyelectrolytes from aqueous solution. The surface of a substrate can have essentially any shape, for example, planar, spherical, rod-shaped, etc. A substrate surface can be regular or irregular. A substrate can be a crystal. A substrate can be a bioactive molecule. Substrates range in size from the nanoscale to the macro-scale. Moreover, a substrate optionally comprises several small subparticles. A substrate can be made of organic material, inorganic material, bioactive material, or a combination thereof. Nonlimiting examples of substrates include silicon wafers; charged colloidal particles, e.g., microparticles of $CaCO_3$ or of melamine formaldehyde; biological cells such as erythrocytes, hepatocytes, bacterial cells, or yeast cells; organic polymer lattices, e.g., polystyrene or styrene copolymer lattices; liposomes; organelles; and viruses. In one embodiment, a substrate is a medical device such as an artificial pacemaker, a cochlear implant, or a stent.

When a substrate is disintegrated or otherwise removed during or after film formation, it is called "a template" (for film formation). Template particles can be dissolved in appropriate solvents or removed by thermal treatment. If, for example, partially cross-linked melamine-formaldehyde template particles are used, the template can be disintegrated by mild chemical methods, e.g., in DMSO, or by a change in pH value. After dissolution of the template particles, hollow multilayer shells remain which are composed of alternating polyelectrolyte layers.

A "capsule" is a polyelectrolyte film in the form of a hollow shell or a coating surrounding a core. The core comprises a variety of different encapsulants, for example, a protein, a drug, or a combination thereof. Capsules with diameters less than about 1 μm are referred to as nanocapsules. Capsules with diameters greater than about 1 μM are referred to as microcapsules.

"Cross linking" means the formation of a covalent bond, or several bonds, or many bonds between two or more molecules.

"Bioactive molecule" means a molecule, macromolecule, or macromolecular assembly having a biological effect. The specific biological effect can be measured in a suitable assay and normalizing per unit weight or per molecule of the bioactive molecule. A bioactive molecule can be encapsulated, retained behind, or encapsulated within a polyelectrolyte film. Nonlimiting examples of a bioactive molecule are a drug, a crystal of a drug, a protein, a functional fragment of a protein, a complex of proteins, a lipoprotein, an oligopeptide, an oligonucleotide, a nucleic acid, a ribosome, an active therapeutic agent, a phospholipid, a polysaccharide, a lipopolysaccharide. As used herein, "bioactive molecule" further encompasses biologically active structures, such as, for example, a functional membrane fragment, a membrane structure, a virus, a pathogen, a cell, an aggregate of cells, and an organelle. Examples of a protein that can be encapsulated or retained behind a polypeptide film are hemoglobin; enzymes, such as for example glucose oxidase, urease, lysozyme and the like; extracellular matrix proteins, for example, fibronectin, laminin, vitronectin and collagen; and an antibody. Examples of a cell that can be encapsulated or retained behind a polyelectrolyte film are a transplanted islet cell, a eukaryotic cell, a bacterial cell, a plant cell, and a yeast cell.

"Biocompatible" means causing no substantial adverse health effect upon oral ingestion, topical application, transdermal application, subcutaneous injection, intramuscular injection, inhalation, implantation, or intravenous injection. For example, biocompatible films include those that do not cause a substantial immune response when in contact with the immune system of, for example, a human being.

"Immune response" means the response of the cellular or humoral immune system to the presence of a substance anywhere in the body. An immune response can be characterized in a number of ways, for example, by an increase in the bloodstream of the number of antibodies that recognize a certain antigen. Antibodies are proteins secreted by B cells, and an immunogen is an entity that elicits an immune response. The human body fights infection and inhibits reinfection by increasing the number of antibodies in the bloodstream and elsewhere.

"Antigen" means a foreign substance that elicits an immune response (e.g., the production of specific antibody molecules) when introduced into the tissues of a susceptible vertebrate organism. An antigen contains one or more epitopes. The antigen may be a pure substance, a mixture of substances (including cells or cell fragments). The term antigen includes a suitable antigenic determinant, autoantigen, self-antigen, cross-reacting antigen, alloantigen, tolerogen, allergen, hapten, and immunogen, or parts thereof, and combinations thereof, and these terms are used interchangeably. Antigens are generally of high molecular weight and commonly are polypeptides. Antigens that elicit strong immune responses are said to be strongly immunogenic. The site on an antigen to which a complementary antibody may specifically bind is called an epitope or antigenic determinant.

"Antigenic" refers to the ability of a composition to give rise to antibodies specific to the composition or to give rise to a cell-mediated immune response.

As used herein, the terms "epitope" and "antigenic determinant" are used interchangeably and mean the structure or sequence of an antigen, e.g., a protein or a designed peptide, which is recognized by an antibody. Ordinarily an epitope will be on the surface of a protein. A "continuous epitope" is one that involves several contiguous amino acid residues, not one that involves amino acid residues that happen to be in contact or in the limited region of space in a folded protein. A "conformational epitope" involves amino acid residues from different portions of the linear sequence of a protein that come into contact in the three-dimensional structure of the protein. For efficient interaction to occur between the antigen and the antibody, the epitope must be readily available for binding. Thus, the epitope or antigenic determinants are present in the antigen's native, cellular environment, or only exposed when denatured. In their natural form they may be cytoplasmic (soluble), membrane associated, or secreted. The number, location and size of the epitopes will depend on how much of the antigen is presented during the antibody making process.

As used herein, a "vaccine composition" is a composition which elicits an immune response in a mammal to which it is administered and which protects the immunized organism against subsequent challenge by the immunizing agent or an immunologically cross-reactive agent. Protection can be complete or partial with regard to reduction in symptoms or infection as compared with a non-vaccinated organism. An immunologically cross-reactive agent can be, for example, the whole protein (e.g., glucosyltransferase) from which a subunit peptide has been derived for use as the immunogen. Alternatively, an immunologically cross-reactive agent can be a different protein, which is recognized in whole or in part by antibodies elicited by the immunizing agent.

As used herein, an "immunogenic composition" is intended to encompass a composition that elicits an immune response in an organism to which it is administered and which may or may not protect the immunized mammal against subsequent challenge with the immunizing agent. In one embodiment, an immunogenic composition is a vaccine composition.

The invention is further illustrated by the following non-limiting examples

EXAMPLES

Testing Protocols

Mice and immunizations: Female C57BL/6J and BALB/c mice, 6-8 weeks of age, were obtained from Jackson Laboratories and housed at NorthEast Life Sciences, New Haven. Mice were acclimated to the environment for at least one week prior to use. Nanoparticles, microparticles, or microcapsules were resuspended in PBS to the desired DP concentration (e.g., 10 µg/100 µl/injection) and sonicated for 10 minutes immediately prior to syringe loading and immunization. Mice were immunized with the suspension in the rear footpad on days 0, 21 and 42. Positive control mice were immunized s.c. with DP in CFA (d0) or IFA (d21, d42); negative control mice were mock immunized with PBS.

ELISA: Mice were bled on days 28 (post-first boost), 49 (post-second boost) and 58 (post-challenge) and sera were harvested for analysis of antibody responses using ELISA plates coated with T1B, T1BT* or B-repeat peptides. For determination of epitope display on nanoparticles, plates were coated with the indicated nanoparticles, blocked, and probed with MAb 2A10 (anti-B repeat). Antibody binding was detected with HRP-labeled goat anti-mouse IgG.

ELISPOT: Mice were sacrificed on days 28, 49, and 58 and spleens were harvested and teased into single-cell suspensions. Unfractionated spleen cells were restimulated with the indicated minimal epitope peptide in IFNγ or IL-5 ELISPOT plates using commercial reagents (BD Biosciences) and plates (Millipore Corporation) and following the manufacturers' instructions. The number of spots on each plate was counted in an AID Viruspot Reader.

PfPb challenge: C57BL/6J or BALB/c mice were immunized on days 0, 21, and 42 as indicated in the Figure descriptions. Mice were bled on day 49 and antibody titers were measured by ELISA as described above. Following the antibody measurement, mice were challenged with PfPb (*Plasmodium bergheii* transfected with the CS gene of *P. falciparum*). The challenge was accomplished by anesthetizing the mice and allowing PfPb-infected mosquitoes to feed on them for 10 minutes. Two days post-challenge, the challenged mice were bled and sacrificed, and liver RNA was extracted for analysis of parasite burden by qPCR.

Transgenic sporozoite neutralization assay (TSNA): The parasite-neutralizing activity of sera in the TSNA was performed by methods known in the art. In brief, a 1:5 dilution of each serum sample was incubated with PfPb parasites (*Plasmodium bergheii* transfected with the CS gene of *P. falciparum*) for 40 minutes on ice. The mixtures were added to wells containing HepG2 cells and incubated at 37° C. for 72 hour. Parasite 18S rRNA levels in each culture were measured by qPCR and compared to a standard curve generated with known amounts of plasmid 18S cDNA. The percent inhibition of parasite growth was calculated by comparison to control wells containing PfPb and HepG2 cells with no serum.

RNA isolation and qPCR: Approximately 40 hours post-challenge, mice were sacrificed and livers were harvested and washed twice with 10 ml sterile PBS. Livers were homogenized in 10 ml TriReagent (Molecular Research Center, cat# TR118) using a polytron homogenizer (Fisher Scientific PowerGen 500) for 1 minute at highest setting. Homogenates were vortexed for 2 minutes and allowed to sit at RT for 10 minutes. The clear homogenate was collected into sterile Eppendorf tubes to which 200 µl of chloroform (Sigma C-0549) was added. Samples were vortexed for 2 minutes, allowed to sit at RT for 15 minutes, then centrifuged at 14,000 rpm at 4° C. for 15 minutes. The aqueous phase (450 µl) was collected into sterile 1.5 ml Eppendorf tubes to which an equal volume of isopropanol (Sigma 405-7) was added. Samples were vortexed for 10 seconds, allowed to sit at RT for 10 minutes, then centrifuged at 14,000 rpm at RT for 10 minutes. The supernatant was decanted and the pellet was washed with 1 ml of 70% EtOH (Sigma E7023), vortexed for 10 seconds, and centrifuged at 14,000 rpm at RT for 10 minutes. The supernatant was decanted and the pellet was dried at RT. Dried pellets were resuspended in 200 µl of DEPC $H_2O$ (Invitrogen cat#750023) for qPCR.

RNA was also isolated from the TriReagent homogenate using the Qiagen RNeasy MiniPrep protocol (Qiagen), and converted to cDNA using iScript RT Supermix (Bio-Rad), each according to manufacturer's protocol. PCR was performed on a CFX96 (Bio-Rad) to determine copy numbers of *P. bergei* 18S rRNA in the liver tissue. Primer sequences used were:

```
                                        (SEQ ID NO: 4)
    forward 5'-AAGCATTAAATAAAGCGAATACATCCTTAC-3'

(SEQ ID NO: 5)
    reverse 5'-GGAGATTGGTTTTGACGTTTATGTG-3'
```

Cycling conditions using iQ SYBR Green Supermix (Bio-Rad) were: 95° C. for 3 min, then [95° C. for 20 sec, 60° C. for 30 sec, 72° C. for 30 sec] repeated 40 times. To determine copy number, a plasmid of known concentration containing *P. bergei* 18S rRNA sequence (NYU) was used to construct a standard curve.

Example 1

Exemplary Peptide Design and Synthesis

Figure 1:
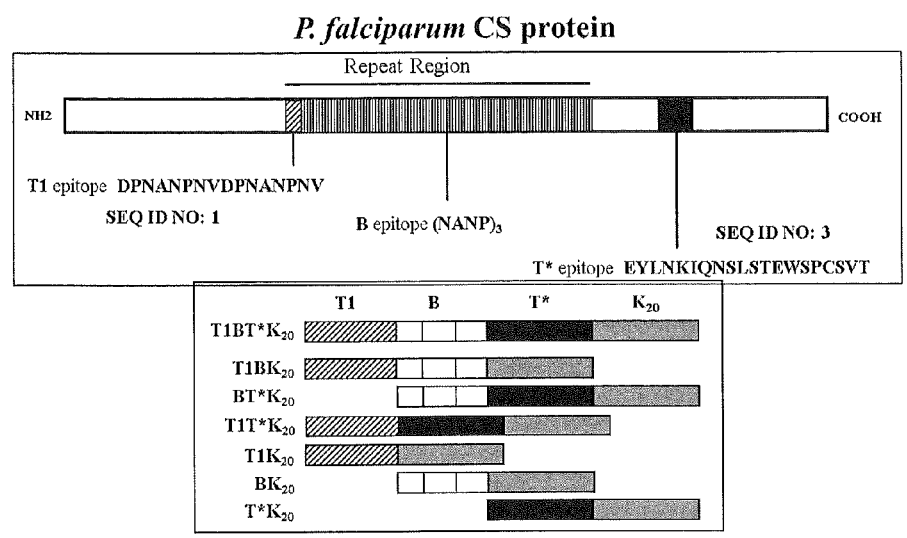

Designed polypeptides were based on the T1BT* multivalent peptide of *P. falciparum* CS. Each combination of one, two, or all three epitopes was modified at the C-terminus with $K_{20}Y$ (SEQ ID NO: 6) to yield designed peptides (DP) for incorporation in LbL particles (FIG. 1). Minimal epitope peptides and DP were synthesized by ACT scientists using standard solid phase peptide chemistry. Peptides were purified by RP-HPLC and quantified by amino acid analysis (data not shown).

```
T1BT*K20Y: (DP-2062)
                                        (SEQ ID NO: 7)
DPNANPNVDPNANPNVNANPNANPNANPEYLNKIQNSLSTEWSPCSVTS

GNGKKKKKKKKKKKKKKKKKKKY

T1K20Y:
                                        (SEQ ID NO: 8)
DPNANPNVDPNANPNVDPNAKKKKKKKKKKKKKKKKKKKY

BK20Y:
                                        (SEQ ID NO: 9)
NANPNANPNANPNANPKKKKKKKKKKKKKKKKKKKY

T*K20Y:
                                        (SEQ ID NO: 10)
EYLNKIQNSLSTEWSPCSVTSGNGKKKKKKKKKKKKKKKKKKKY

T1BK20Y:
                                        (SEQ ID NO: 11)
DPNANPNVDPNANPNVNANPNANPNANPKKKKKKKKKKKKKKKK

KKKY

T1T*K20Y:
                                        (SEQ ID NO: 12)
DPNANPNVDPNANPNVEYLNKIQNSLSTEWSPCSVTSGNGKKKKKKKK

KKKKKKKKKKY

BT*K20Y:
                                        (SEQ ID NO: 13)
NANPNANPNANPEYLNKIQNSLSTEWSPCSVTSGNGKKKKKKKKKKKK

KKKKKKY
```

Example 2

Procedure for Fabrication of LBL Nanoparticles $CaCO_3$ cores were obtained from NanoMaterials Technology Pte Ltd, Singapore (50 nm, solid, cubic). PLL and PGA were obtained from Sigma-Aldrich, USA. PLL, PGA and DP were dissolved in 10 mM HEPES, pH 7.4. Oppositely charged polypeptides were allowed to self-assemble into a multilayer film on $CaCO_3$ nanoparticle cores in successive adsorption steps. Briefly, PLL, PGA and DP (where indicated) were dissolved to 1 mg/ml in 10 mM HEPES, pH 7.4, and filtered through a 0.22 µm filter. $CaCO_3$ nanoparticle cores were washed three times with endotoxin-free water and centrifugation at 16,000×g for 1 minute in a microcentrifuge. Nanoparticle cores were resuspended to 6% (w/v) in 1 mg/ml PGA as the first layer. At neutral pH, PGA exhibits a net negative charge while the $CaCO_3$ particles are net positive, thus enabling electrostatic interaction and successful deposition of the first layer. The mixture was incubated for 10 minutes at room temperature, then washed twice with 10 mM HEPES buffer and centrifugation at 48,700×g for 1 minute (TL-100 Ultracentrifuge, Beckman). For second layer deposition, the nanoparticles were resuspended to 6% (w/v) in 1 mg/ml PLL (positive charge) and processed as for the first layer. Each subsequent layer was deposited by the same method, using PGA and PLL in alternating layers; where indicated, DP (positive charge) was used for the indicated layer. Following the final layer deposition, the mature particles were washed and stored as damp pellets at 4° C. or RT until use. Particle integrity and quality control were monitored using the methods described in Table 1, and specific constructs are identified in Table 2.

TABLE 1

QC criteria and methodologies employed

| Parameter | Method |
|---|---|
| Size and dispersity | dynamic light scattering |
| Endotoxin | commercial LAL kit |
| PGA/PLL concentration | amino acid analysis upon resuspension |
| DP concentration | amino acid analysis upon resuspension |
| Stability @ 37° C. | amino acid analysis at selected time points |

TABLE 2

List of nanoparticles

| ACT # | DP (DP #) | Particle size <400 nm |
|---|---|---|
| 1051-02 | T1BT*$K_{20}$Y (SEQ ID NO: 7) (2062) | 143 |
| 1052-02 | B$K_{20}$Y (SEQ ID NO: 9) (2060) | 165 |
| 1056-02 | T1T*$K_{20}$Y (SEQ ID NO: 12) (2063) | 170 |
| 1129-01 | T*$K_{20}$Y (SEQ ID NO: 10) (2057) | 143 |
| 1130-01 | T1$K_{20}$Y (SEQ ID NO: 8) (2059) | 163 |
| 1131-01 | T1B$K_{20}$Y (SEQ ID NO: 11) (2119) | 123 |
| 1132-01 | BT*$K_{20}$Y (SEQ ID NO: 13) (2120) | 143 |

Example 3

Antibody Response Elicited by Nanoparticles

Figure 2:
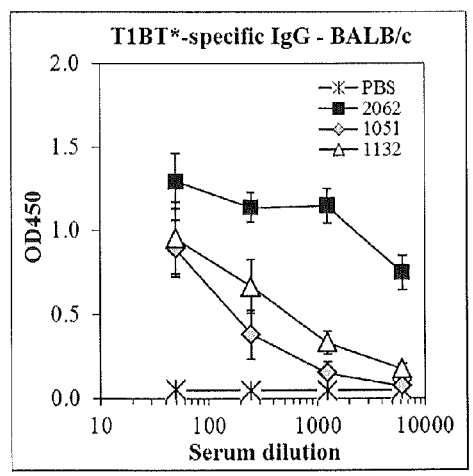
Figure 3:
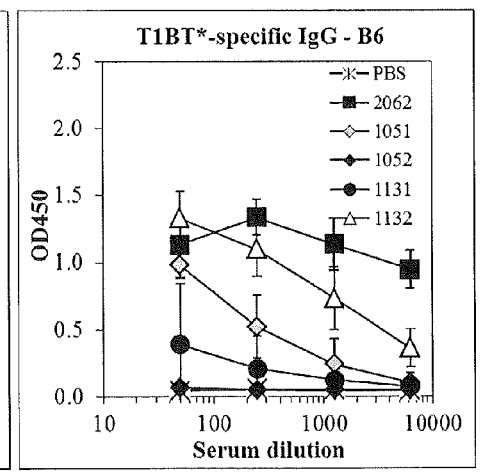

BALB/c mice were immunized via f.p. on days 0, 21 and 42 with PBS (negative control), 10 μg of DP in CFA (positive control), or 10 μg of nanoparticles containing T* epitope (ACT-1051 (SEQ ID NO: 7), ACT-1056 (SEQ ID NO: 12), ACT-1129 (AEQ ID NO: 10) and ACT-1132 (SEQ ID NO: 13)). C57BL/6 mice were immunized via f.p. on days 0, 21 and 42 with PBS (negative control), 10 μg of DP in CFA (positive control), or 10 μg of nanoparticles containing B epitope (ACT-1052 (SEQ ID NO: 9)) or T1 epitope (ACT-1051 (SEQ ID NO: 7), ACT-1056 (SEQ ID NO: 12), ACT-1130 (SEQ ID NO: 8), and ACT-1131 (SEQ ID NO: 11)). All mice were bled on day 49 (7 days post second boost) and three mice per group were sacrificed for ELISPOT analysis. ELISA results demonstrate that ACT-1051 (T1BT*$K_{20}$Y; SEQ ID NO: 7) and ACT-1132 (BT*$K_{20}$Y; SEQ ID NO: 13) induced T1BT*-specific antibody responses in both strains of mice; ACT-1131 (T1B$K_{20}$Y; SEQ ID NO: 11) induced modest T1BT*-specific antibody response in C57BL/6 mice, while ACT-1052 (B$K_{20}$Y; SEQ ID NO: 9) failed to elicit detectable antibody responses (FIGS. 2 and 3). None of the antisera recognized the B repeat epitope in ELISA (data not shown)

Figure 4:
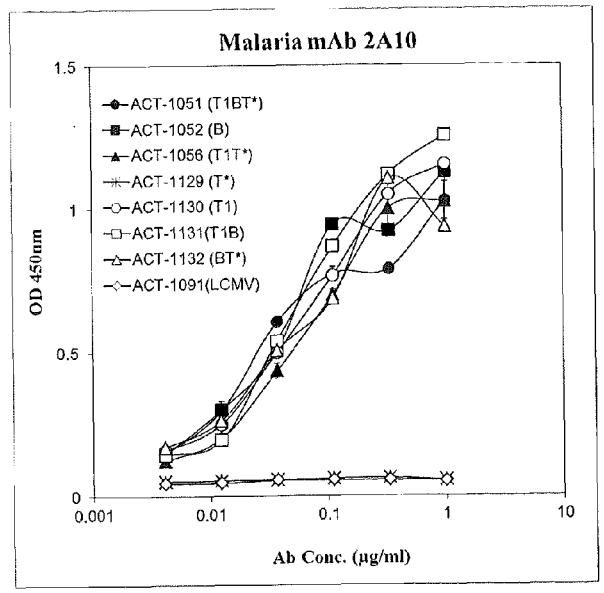

It is possible that the lack of antibody response to the B repeat is due to improper display of the epitope in the particles. This possibility was addressed by coating ELISA plates with the indicated nanoparticles and probing with serial dilutions of mAb 2A10, specific for the B repeat (NANP sequence). The results in FIG. 4 show that repeat-specific mAb reacted with all nanoparticles that contain the T1 or B repeat epitopes, but not with nanoparticles containing only T* or an irrelevant epitope derived from LCMV. These results suggest the lack of B repeat antibody responses is not due to insufficient display of the epitope on the nanoparticles.

Example 4

T-Cell Responses with Nanoparticles

Figure 5:
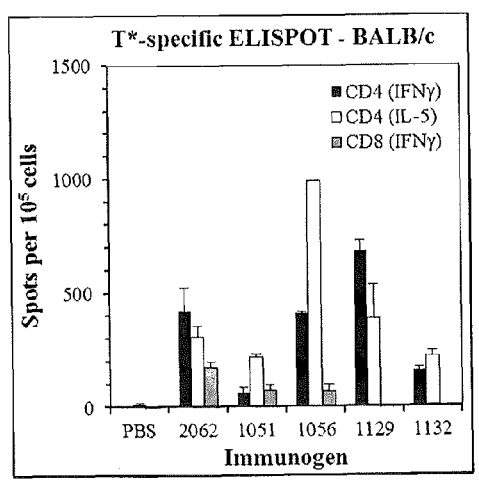
Figure 6:
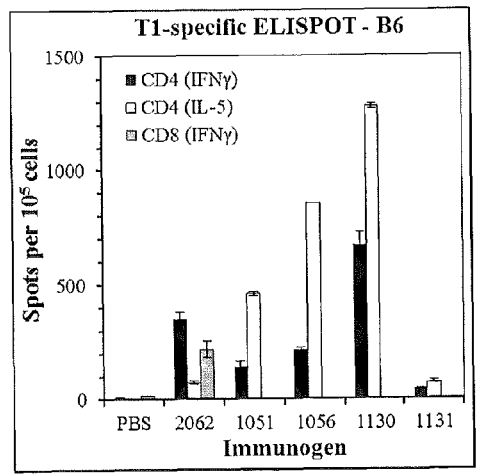

To determine the specificity of the CD4+ and CD8+ responses of the mice depicted in FIGS. 2 and 3, ELISPOT responses of enriched CD4+ and CD8+ T-cells against T1 or T* were tested. On day 49, three mice per group were sacrificed, spleen cells were harvested and fractionated into CD4+ or CD8+ populations using magnetic bead enrichment and the autoMACS cell sorter; purity of each population was greater than 90% (data not shown). Cells were restimulated in IL-5 or IFNγ ELISPOT plates with the indicated peptides. The results in FIGS. 5 and 6 show that three immunizations with nanoparticle ACT-1056 (T1T*$K_{20}$Y (SEQ ID NO: 12)) or ACT-1129 (T*$K_{20}$Y (SEQ ID NO: 10)) elicited strong T*-specific CD4+ T-cell responses in BALB/c mice, while three immunizations with nanoparticle ACT-1056 (T1T*$K_{20}$Y (SEQ ID NO: 12)) or ACT-1130 (T1$K_{20}$Y (SEQ ID NO: 8)) elicited strong T1-specific CD4+ T-cell responses in C57BL/6 mice. In most cases, the T-cell response was biased toward IL-5 (Th2) over IFNγ (Th1). All constructs induced weak CD8+ T-cell responses in both strains of mice.

Example 5

PfPb Challenge with Nanoparticles

Figure 7:
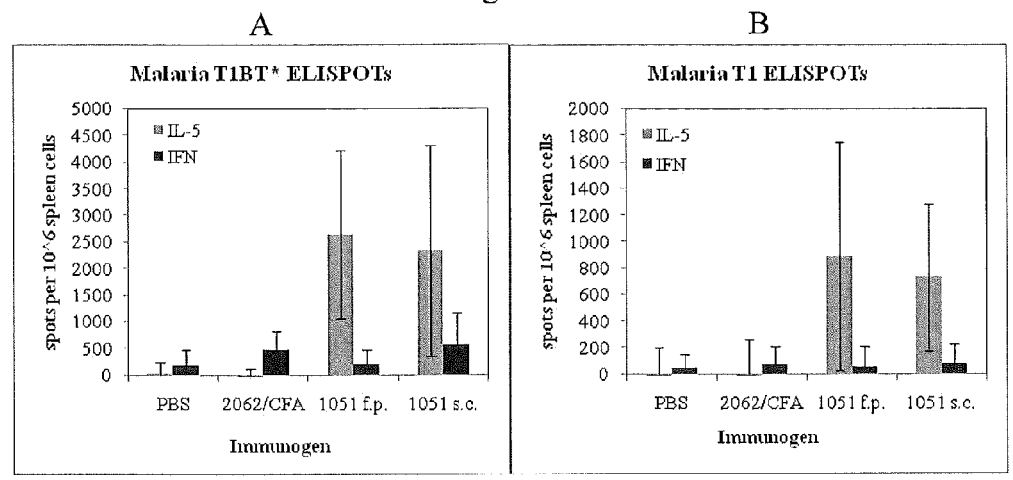

In a separate experiment, seven mice per group were immunized with nanoparticle ACT-1051 or its designed peptide ACT-2062 (T1BT*$K_{20}$Y (SEQ ID NO: 7)), then challenged with PfPb. The mice were sacrificed two days post-challenge and liver RNA was extracted for analysis of parasite burden by qPCR (NYU). In addition, the spleens were harvested and assayed for T-cell responses to T1BT* and T1 peptides in IL-5 and IFNγ ELISPOTs. FIG. 7 shows that the immunized mice mounted a weak INFγ response to both the full length T1BT* and the T1 epitope. Surprisingly, a strong IL-5 response was detected in the mice immunized with nanoparticle. As neither the PBS nor 2062/CFA groups show this response, the IL-5 production is not a result of the infection alone but appears to be associated with nanoparticle immunization prior to the infection.

Figure 8:
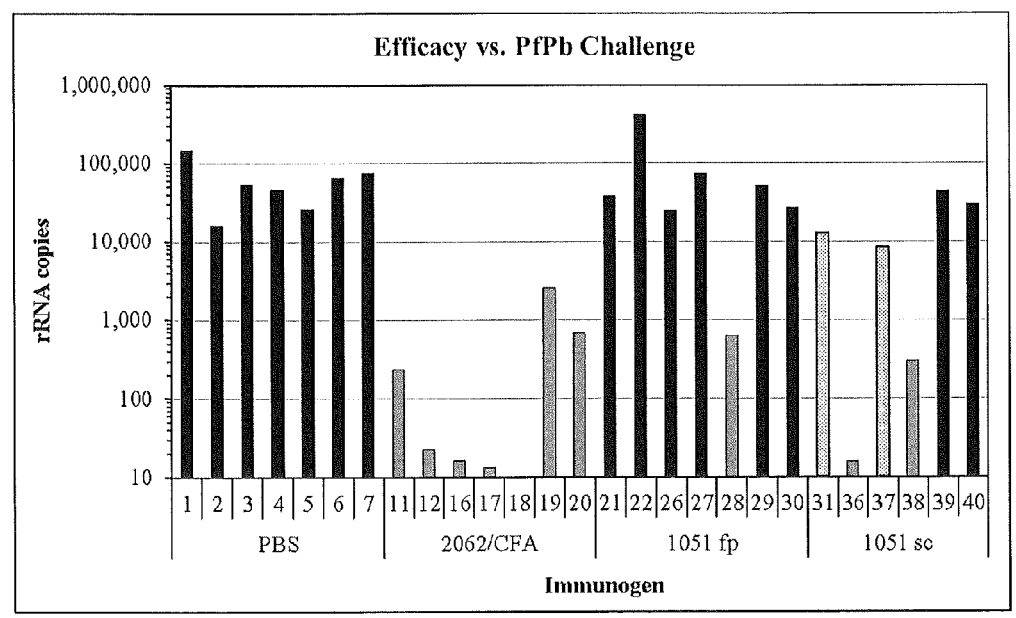

The liver RNA extracted from the challenged mice was subjected to qPCR analysis of parasite burden. The results in FIG. 8 show that all of the 2062/CFA-immunized mice were protected from PfPb challenge as evidenced by >90% reduction in parasite RNA levels compared to the average of the PBS-treated mice. It is encouraging that at least three of the immunized mice (one in the f.p. group and two in the s.c. group) exhibited similar levels of protection, and two more in the s.c. group exhibited marginal protection (>80% reduction). However, when the individual parasite burdens were compared to immune responses (antibody titers and ELISPOT responses), no clear immune correlate of protection could be found (data not shown).

Example 6

Fabrication of Microparticles

Peptide ACT-2062 (T1BT*$K_{20}$Y (SEQ ID NO: 7)) was synthesized using standard solid phase peptide chemistry, purified by RP-HPLC and quantified by amino acid analysis.

$CaCO_3$ cores were obtained from PlasmaChem GmbH, Germany (3 μm, mesoporous, spherical). PLL and PGA were obtained from Sigma-Aldrich, USA. PLL, PGA and ACT-2062 were dissolved in 10 mM HEPES, pH 7.4. LbL particles were fabricated essentially as for the nanoparticles. After assembling the 7 base layers with PGA and PLL, the film was cross-linked using 200 mM EDC and 50 mM sulfo-NHS in 200 mM phosphate buffer, pH 6.5. The particles were washed twice with 10 mM HEPES buffer to remove any residual reagent. The DP (ACT-2062, T1BT*$K_{20}$Y (SEQ ID NO: 7)) was added as the $8^{th}$ layer to generate microparticle ACT-1140. In microparticle ACT-1141, the 7 base layers were crosslinked prior to depositing the DP. Microcapsule ACT-1142 was prepared by treating ACT-1141 with 0.5 M EDTA to dissolve the $CaCO_3$ core prior to depositing the DP. The mature particles and capsules were washed and stored as damp pellets at 4° C. or RT until use.

Example 7

Immunogenicity of Microparticles and Microcapsules

Figure 9:
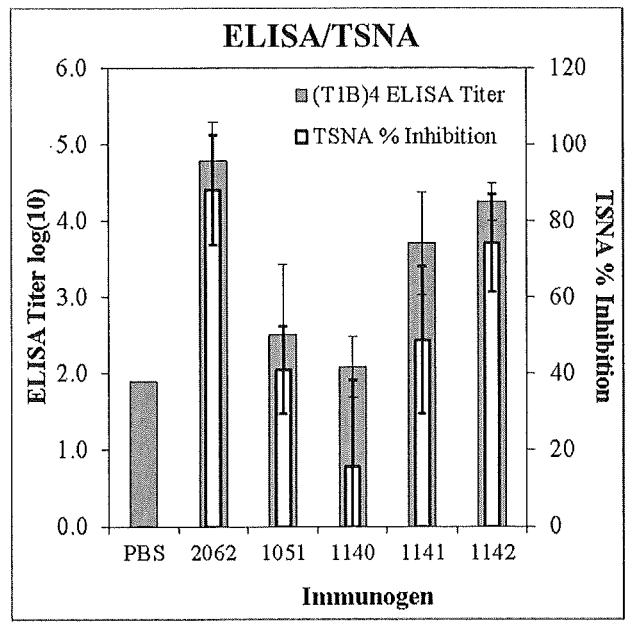
Figure 10:
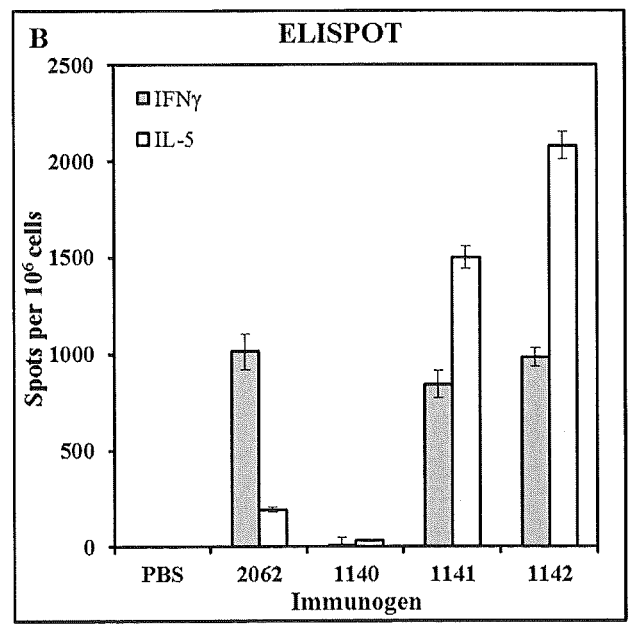

C57BL/6J mice were immunized with MP-1140, MP-1141, or MC-1142, each loaded with DP 2062 (T1BT*$K_{20}$Y; SEQ ID NO: 7). Antibody responses were tested by ELISA and TSNA, while T-cell responses were tested by ELISPOT. MP-1141 and MC-1142 were the most potent LbL constructs, eliciting antibody titers (FIG. 9) and IFNγ+ responses (FIG. 10) comparable to the positive control mice. FIG. 9 also shows that the T1B ELISA results correlate with the level of functional antibody activity measured in the TSNA ($r^2$=0.79, P=0.0004 by Pearson Correlation Coefficient analysis of individual serum titers in both assays), demonstrating the utility of the ELISA as a rapid screening method for measuring functional anti-T1B antibody responses.

Example 8

Efficacy of Microparticles and Microcapsules

Mice were immunized with MP-1141 or MC-1142 and challenged by exposure to bites of PfPb-infected mosquitoes. Forty hours post-challenge, parasite burden in livers was monitored by quantifying *P. berghei* 18S rRNA levels via qPCR. Protection is defined as ≥90% reduction in parasite burden compared to naïve, challenged mice. Immunization with MP-1141 protected 8 of 10 mice and resulted in a 94% reduction in average parasite burden in the treatment group (P<0.05, Wilcoxon rank sum test), comparable to control mice immunized with DP 2062 in Freund's adjuvant (FIG. 11). Immunization with MC-1142 protected half of the mice but did not result in a significant reduction in the group average parasite burden compared to PBS control.

Figure 12:
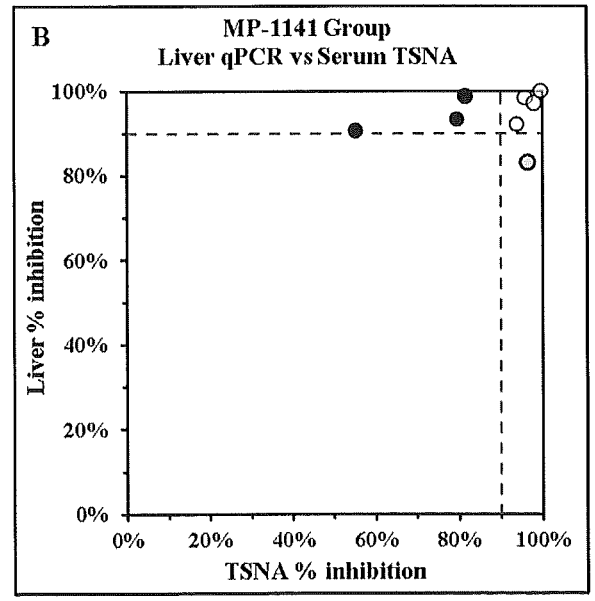
FIG. 12 shows a comparison of in vivo protection from parasite challenge and in vitro neutralizing activity for eight randomly-selected individual sera from FIG. 11 for the MP-1141 group.
Figure 13:
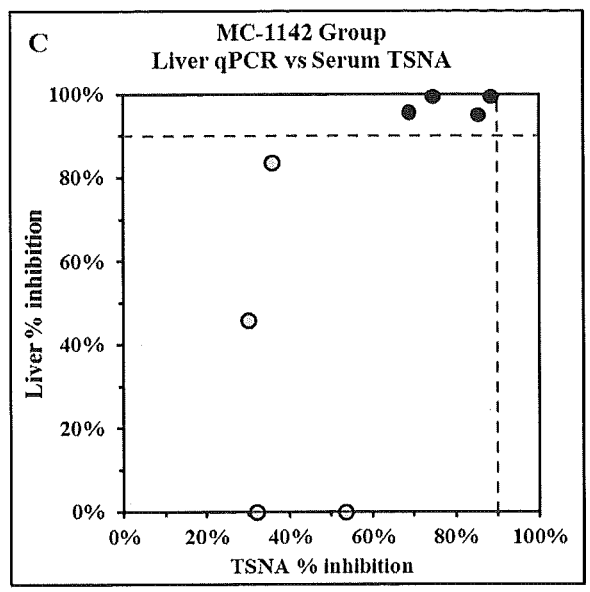
FIG. 13 shows a comparison of in vivo protection from parasite challenge and in vitro neutralizing activity for eight randomly-selected individual sera from FIG. 11 for the MP-1142 group.

Sera collected from the mice prior to challenge were tested in the TSNA to measure parasite-neutralizing activity that effectively blocked sporozoite invasion of human hepatoma cells in vitro, defined as >90% reduction of parasite rRNA levels in HepG2 cells measured by qPCR. A comparison of TSNA activity with in vivo efficacy showed that efficacy was associated with potent neutralizing antibody activity in half of the MP-1141-immunized mice (FIG. 12, open circles). However, there were several mice in both immunized groups that were protected from parasite challenge in vivo while mounting only modest neutralizing antibody responses (FIGS. 12 and 13, black circles), suggesting that cellular mechanisms may also be involved in protection.

Example 9

T-Cell Responses Elicited by Microparticles

On the same days that sera were collected for ELISA (FIGS. 12 and 13), spleen cells were harvested and stimulated with T1B peptide in IFNγ and IL-5 ELISPOT plates. Mice immunized with ACT-1141 or ACT-1142 produced both Th1 (IFNγ) and Th2 (IL-5) responses while mice immunized with DP 2062 in adjuvant produced a response biased toward Th1 (IFNγ) (FIG. 14).

Example 10

Role of Cellular Immunity in Efficacy of LbL Particles

The detection of IFNγ-secreting cells in ELISPOT (FIG. 10) suggests potential activation of cytotoxic effector T-cells following LbL particle immunization, as found previously. The generation of malaria-specific cytotoxic effector cell responses was examined in an in vivo CTL assay using BALB/c mice since C57BL/6J mice fail to develop strong CTL responses to CS protein and there is a known $H-2^d$ restricted CD8+ T-cell epitope contained within the T* epitope. Mice were immunized with PBS or MP-1141, and 7 days later were depleted of CD4+, CD8+, or both T-cell phenotypes by administration of the relevant monoclonal antibodies. The next day, in vivo CTL activity was measured. FIG. 15 shows that a modest level of killing of T*-loaded target cells was detected in the immunized mice with intact T-cell populations. Depletion of CD8+ cells did not decrease the in vivo CTL activity while depletion of CD4+ cells completely prevented effector activity, indicating that immunization with LbL MP bearing the T1BT* antigen elicits CD4+ cytotoxic effector cells, in agreement with published results demonstrating CD4+ effector activity in human volunteers.

Figure 16:
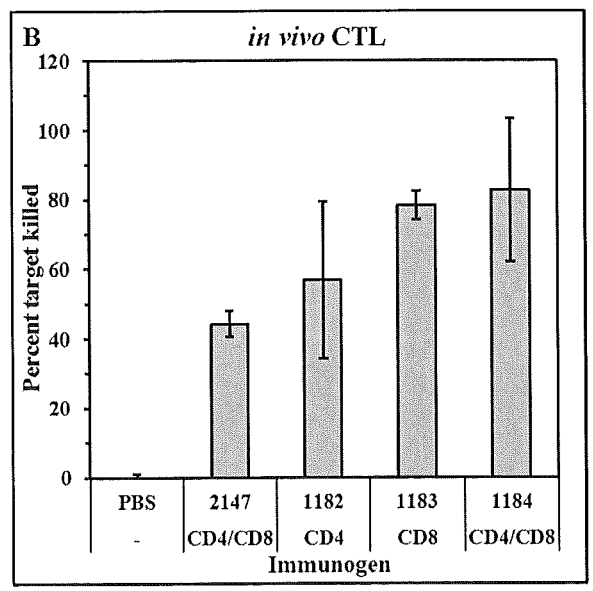
Figure 17:
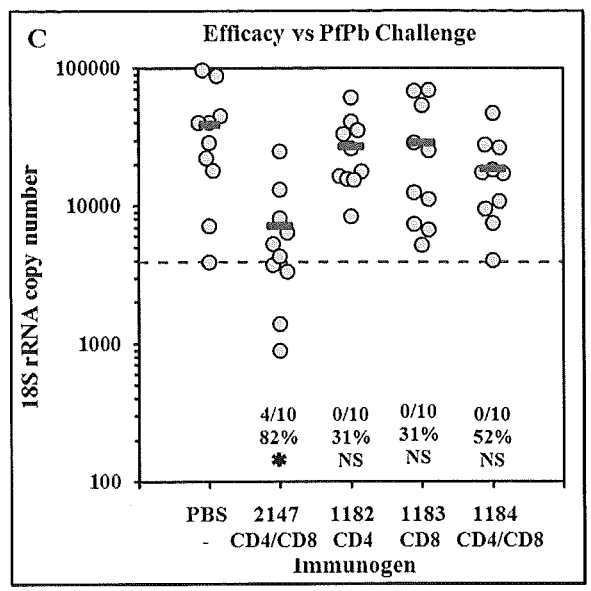

In light of the T-cell responses detected in ELISPOT (FIG. 10) and in vivo CTL assay (FIG. 15), and the apparent discordance between efficacy and TSNA titers in several of the immunized mice (FIGS. 12 and 13), we examined the contribution of cellular immunity to efficacy of LbL microparticles. To test the efficacy of cellular responses alone, in the absence of T1B-specific antibody responses, we constructed MP loaded with T-cell epitopes from the CS protein of *P. berghei*, the mouse pathogen (Table 3). BALB/c were used in this study since both the CD4+ and CD8+ T-cell epitopes are recognized in H-$2^d$ mice. Mice were immunized on days 0 and 28 with MP containing *P. berghei* CD4+ T-cell epitopes (MP-1182), CD8+ T-cell epitopes (MP-1183), a fusion peptide containing both T-cell epitopes (MP-1184), or DP fusion peptide in Freund's adjuvant. On day 35, an in vivo CTL experiment was performed using target cells loaded with the immunizing epitope(s). Immunization with MP loaded with either *P. berghei* T-cell epitope elicited effector activity against target cells loaded with the immunizing peptide (FIG. 16). However, the CTL activity was not sufficient to protect the mice against challenge with PfPb sporozoites which express the *P. berghei* T-cell epitopes (FIG. 17), suggesting that the efficacy reported in FIG. 11 was antibody-mediated.

TABLE 3

Microparticles loaded with T-cell epitopes from the CS protein of *P. berghei*

| Particle # | DP # | Epitope(s) and source | Sequence |
|---|---|---|---|
| MP-1182 | DP-2145 | CD4 Pb | SEQ ID NO: 14 |
| MP-1183 | DP-2146 | CD8 Pb | SEQ ID NO: 15 |
| MP-1184 | DP-2147 | CD8:CD4 Pb | SEQ ID NO: 16 |

SEQ ID NO: 14
LEFVKQIRDSITEEWSQCNVKKKKKKKKKKKKKKKKKKKY
SEQ ID NO: 15
KNNNNDDSYIPSAEKILEFVKKKKKKKKKKKKKKKKKKKY
SEQ ID NO: 16
KNNNNDDSYIPSAEKILEFVKQIRDSITEEWSQCNVKKKKKKKKKKKKKKKKKKKKY

Example 11

Immunogenicity of Pam3Cys.T1B Malaria Microparticles

Clinical trials of malaria peptide vaccines have demonstrated that adjuvants can significantly increase antibody and cellular responses, but frequently at the cost of increased reactogenicity. The use of TLR agonists that more precisely target innate immunity may help avoid excessive inflammatory responses associated with potent adjuvants. $Pam_3Cys$, a synthetic lipopeptide TLR2 agonist, is an especially attractive innate immune stimulator for the LbL approach since it can be incorporated directly into DP. A series of DP containing various T1B configurations was synthesized (see Table 4). The sequences of the T1 and B *Plasmodium falciparum* circumsporozoite protein antigens are given below:

T1: DPNANPNVDPNANPNV (SEQ ID NO: 1)

B: NANP (SEQ ID NO: 2)

$CaCO_3$ cores were obtained from PlasmaChem GmbH, Germany (3 μm, mesoporous, spherical). PLL and PGA were obtained from Sigma-Aldrich, USA. PLL, PGA and ACT-2062 (T1BT*$K_{20}$Y: DPNANPNVDPNANPNVNAN-PNANPNANPEYLNKIQNSLSTEWSPCSVTSGNGK KKKKKKKKKKKKKKKKKKKY (SEQ ID NO: 7)) were dissolved in 10 mM HEPES, pH 7.4. LbL particles were fabricated essentially as for the nanoparticles. After assembling the 7 base layers with PGA and PLL, the film was cross-linked using 200 mM EDC and 50 mM sulfo-NHS in 200 mM phosphate buffer, pH 6.5. The particles were washed twice with 10 mM HEPES buffer to remove any residual reagent. The DP was added as the $8^{th}$ layer to generate the microparticles listed in Table 4. The mature particles and were washed and stored as damp pellets at 4° C. or RT until use.

The N-terminus of DP-2163 ($T1_3B_5$ Pf) was extended during solution phase synthesis by adding a serine-lysine-lysine-lysine-lysine spacer followed by N-terminal coupling of a Pam3-modified cysteine residue, thus incorporating the TLR2 ligand Pam3Cys to yield DP-2167 ($Pam3.T1_3B_5$ Pf).

TABLE 4

List of microparticles

| Particle # | DP # | Epitope(s) and source | Sequence |
|---|---|---|---|
| MP-1140 MP-1141 MC-1142 | DP-2062 | T1BT* Pf | SEQ ID NO: 7 |
| MP-1167 | DP-2163 | $T1_3B_5$ Pf | SEQ ID NO: 17 |
| MP-1164 | DP-2167 | $Pam3.T1_3B_5$ Pf | $Pam_3$-SEQ ID NO: 17 |

SEQ ID NO: 17 (SKKKK(NANPNVDP)$_3$(NANP)$_5$K$_{20}$Y)
SKKKKNANPNVDPNANPNVDPNANPNVDPNANPNANPNANPNANPNANPKKKKKKKK
KKKKKKKKKKKY

Figure 18:
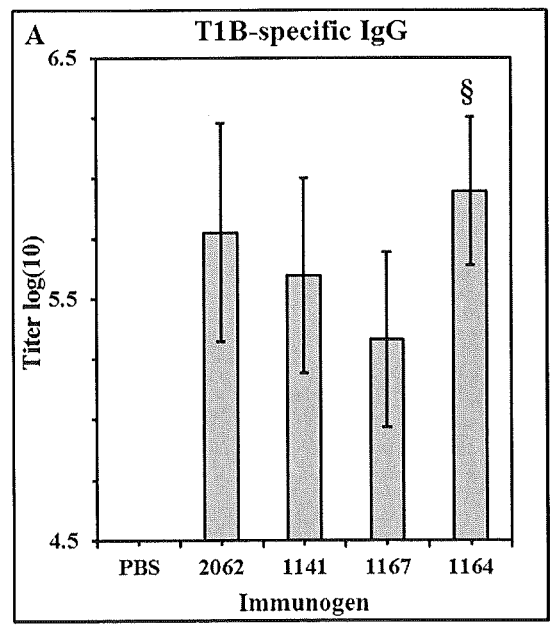
Figure 19:
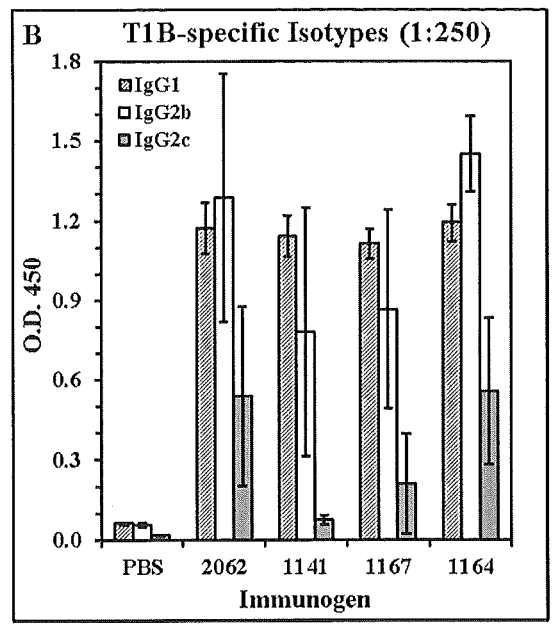
Figure 20:
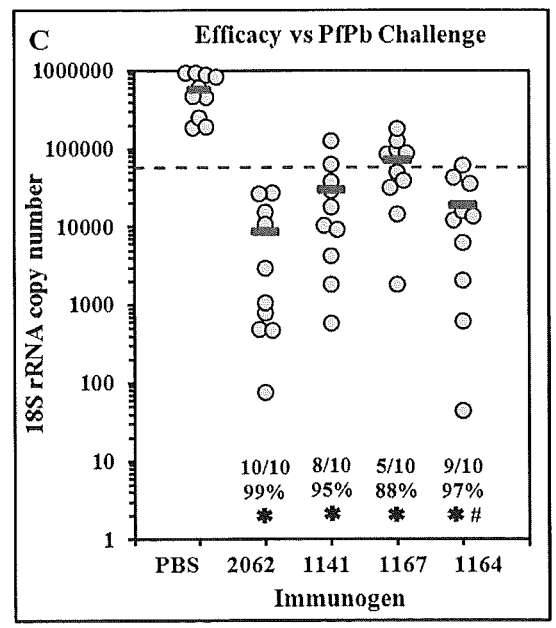

C57BL/6 mice were immunized with MP-1141, MP-1167, or MP-1164; mice immunized with PBS or with DP-2062 (T1BT* (SEQ ID N: 6)) in CFA were included as positive controls. ELISA analysis of sera collected on day 28 shows that MP-1164 containing the $Pam_3Cys$-modified DP was comparable to the positive control DP-2062 (T1BT*) in Freund's adjuvant and statistically more potent than MP-1167 containing the same DP without $Pam_3Cys$ (P=0.02, Wilcoxon rank sum test) (FIG. 18). MP-1164 also yielded an antibody isotype profile identical to that in the positive control group, including the Th1-associated IgG2c isotype that was minimally induced by MP-1167 or MP-1141 (FIG. 19), each of which lacks $Pam_3Cys$. The $Pam_3Cys$-modified MP-1164 was as efficacious as DP 2062 peptide/CFA positive control group, protecting 90% of the mice from liver stage infection (FIG. 20). Protection correlated with neutralizing antibody most strongly in the MP-1164 group (data not shown), modestly in the MP-1141 group (data not shown), and weakly in the MP-1167 group (data not shown). Thus, a simple $Pam_3Cys$ modification of the DP yields an improved LbL vaccine that elicits more potent antibody responses and provides a higher level of protection from parasite challenge.

The use of the terms "a" and "an" and "the" and similar referents (especially in the context of the following claims) are to be construed to cover both the singular and the plural, unless otherwise indicated herein or clearly contradicted by context. The terms first, second, etc., as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

---

The invention claimed is:

1. A composition comprising
a first multilayer film comprising a plurality of oppositely charged polyelectrolyte layers, wherein one of the polyelectrolyte layers in the multilayer film comprises a first antigenic polypeptide polyelectrolyte,
   wherein the first antigenic polypeptide comprises a *Plasmodium falciparum* circumsporozoite T1BT* epitope covalently linked to one or two surface adsorption regions at the C-terminus and/or the N-terminus of the polypeptide, wherein at least one of the surface adsorption regions comprises eight negatively or positively charged amino acid residues,
   wherein the polyelectrolytes in the multilayer film comprise a polycationic material or a polyanionic material having a molecular weight of greater than 1,000 and at least 5 charges per molecule,
   wherein the first multilayer film is deposited on a core nanoparticle or microparticle, or is in the form of a nanocapsule or microcapsule prepared by dissolving the core particle,
   wherein the first multilayer film retains more than half of its polyelectrolytes when incubated in phosphate buffered saline at 37° C. for 24 hours.

2. The composition of claim 1, wherein the first multilayer film further comprises a TLR ligand.

3. The composition of claim 2, wherein the TLR ligand is covalently linked to the first antigenic polypeptide.

4. The composition of claim 1, further comprising a second multilayer film comprising a plurality of oppositely charged polyelectrolyte layers, wherein one of the layers in the second multilayer film comprises a second antigenic polyelectrolyte,
   wherein the second antigenic polyelectrolyte comprises a *Plasmodium falciparum* circumsporozoite T1, B or T* epitope covalently linked to a second polyelectrolyte, wherein the first and second antigenic polyelectrolytes comprise different *Plasmodium falciparum* circumsporozoite epitopes.

5. The composition of claim 4, wherein the first and second polyelectrolytes are polypeptides.

6. The composition of claim 4, wherein the first and second multilayer films are deposited onto core particles.

7. The composition of claim 4, wherein the first and/or second multilayer film further comprises a TLR ligand.

8. The composition of claim 7, wherein the TLR ligand is covalently linked to the first and/or second antigenic polyelectrolyte.

9. The composition of claim 4, further comprising a third multilayer film comprising a plurality of oppositely charged polyelectrolyte layers, wherein one of the layers in the third multilayer film comprises a third antigenic polyelectrolyte,
   wherein the third antigenic polyelectrolyte comprises a *Plasmodium falciparum* circumsporozoite T1, B or T* epitope covalently linked to a third polyelectrolyte, wherein the first, second and third antigenic polyelectrolytes comprise different *Plasmodium falciparum* circumsporozoite epitopes.

10. The composition of claim 9, wherein the first, second, and third polyelectrolytes are polypeptides.

11. The composition of claim 9, wherein the first, second, and third multilayer films are deposited onto core particles.

12. The composition of claim 9, wherein the first, second and/or third multilayer film further comprises a TLR ligand.

13. The composition of claim 12, wherein the TLR ligand is covalently linked to the first, second and/or third antigenic polyelectrolyte.

14. A method of eliciting an immune response in a vertebrate organism comprising administering into the vertebrate organism the composition of claim 1.

15. The composition of claim 1, wherein the multilayer film is covalently crosslinked.

16. The composition of claim 15, wherein the covalent crosslinks are amide bonds involving amino acid side chain functional groups.

17. The composition of claim 1, wherein the first antigenic polypeptide has a magnitude of net charge per residue of greater than or equal to 0.2 at pH 7.0.

18. The composition of claim 1, wherein the composition provides >90% reduction of PfPb (*Plasmodium bergheii* transfected with the circumsporozoite gene of *P. falciparum*) parasite rRNA levels in HepG2 cells measured by qPCR in a transgenic sporozoite neutralization assay (TSNA) performed on a 1:5 dilution of serum from C57BL/6J or BALB/c mice immunized on days 0, 21, and 42 with the composition, wherein the serum is harvested on day 49.

19. The composition of claim 1, wherein the composition produces T1BT*-specific IgG titers, a specific CD4+ T-cell response, or both, in BALB/c or C57BL/6 mice immunized with the compositions.

* * * * *

UNITED STATES PATENT AND TRADEMARK OFFICE
CERTIFICATE OF CORRECTION

| | |
|---|---|
| PATENT NO. | : 9,433,671 B2 |
| APPLICATION NO. | : 13/827469 |
| DATED | : September 6, 2016 |
| INVENTOR(S) | : Thomas J. Powell |

It is certified that error appears in the above-identified patent and that said Letters Patent is hereby corrected as shown below:

In the Specification

In Column 1, at Line 10, insert:

--STATEMENT REGARDING FEDERALLY SPONSORED RESEARCH & DEVELOPMENT
This invention was made with government support under AI091089 awarded by the National Institutes of Health. The government has certain rights in the invention.--

Signed and Sealed this
Seventeenth Day of April, 2018

Andrei Iancu
*Director of the United States Patent and Trademark Office*

SEQUENCE LISTING

```
<160> NUMBER OF SEQ ID NOS: 17

<210> SEQ ID NO 1
<211> LENGTH: 16
<212> TYPE: PRT
<213> ORGANISM: Plasmodium falciparum

<400> SEQUENCE: 1

Asp Pro Asn Ala Asn Pro Asn Val Asp Pro Asn Ala Asn Pro Asn Val
1               5                   10                  15

<210> SEQ ID NO 2
<211> LENGTH: 4
<212> TYPE: PRT
<213> ORGANISM: Plasmodium falciparum

<400> SEQUENCE: 2

Asn Ala Asn Pro
1

<210> SEQ ID NO 3
<211> LENGTH: 20
<212> TYPE: PRT
<213> ORGANISM: Plasmodium falciparum

<400> SEQUENCE: 3

Glu Tyr Leu Asn Lys Ile Gln Asn Ser Leu Ser Thr Glu Trp Ser Pro
1               5                   10                  15

Cys Ser Val Thr
            20

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
aagcattaaa taaagcgaat acatccttac                                           30

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
```

```
ggagattggt tttgacgttt atgtg                                    25
```

\<210\> SEQ ID NO 6
\<211\> LENGTH: 21
\<212\> TYPE: PRT
\<213\> ORGANISM: Artificial Sequence
\<220\> FEATURE:
\<223\> OTHER INFORMATION: Designed peptide

\<400\> SEQUENCE: 6

```
Lys Lys Lys Lys Lys Lys Lys Lys Lys Lys Lys Lys Lys Lys Lys
1               5                   10                  15

Lys Lys Lys Lys Tyr
            20
```

\<210\> SEQ ID NO 7
\<211\> LENGTH: 73
\<212\> TYPE: PRT
\<213\> ORGANISM: Artificial Sequence
\<220\> FEATURE:
\<223\> OTHER INFORMATION: Designed peptide

\<400\> SEQUENCE: 7

```
Asp Pro Asn Ala Asn Pro Asn Val Asp Pro Asn Ala Asn Pro Asn Val
1               5                   10                  15

Asn Ala Asn Pro Asn Ala Asn Pro Asn Ala Asn Pro Glu Tyr Leu Asn
            20                  25                  30

Lys Ile Gln Asn Ser Leu Ser Thr Glu Trp Ser Pro Cys Ser Val Thr
        35                  40                  45

Ser Gly Asn Gly Lys Lys Lys Lys Lys Lys Lys Lys Lys Lys
    50                  55                  60

Lys Lys Lys Lys Lys Lys Lys Lys Tyr
65                  70
```

\<210\> SEQ ID NO 8
\<211\> LENGTH: 41
\<212\> TYPE: PRT
\<213\> ORGANISM: Artificial Sequence
\<220\> FEATURE:
\<223\> OTHER INFORMATION: Designed peptide

\<400\> SEQUENCE: 8

```
Asp Pro Asn Ala Asn Pro Asn Val Asp Pro Asn Ala Asn Pro Asn Val
1               5                   10                  15

Asp Pro Asn Ala Lys Lys Lys Lys Lys Lys Lys Lys Lys Lys
            20                  25                  30

Lys Lys Lys Lys Lys Lys Lys Lys Tyr
        35                  40
```

\<210\> SEQ ID NO 9
\<211\> LENGTH: 37
\<212\> TYPE: PRT
\<213\> ORGANISM: Artificial Sequence
\<220\> FEATURE:
\<223\> OTHER INFORMATION: Designed peptide

\<400\> SEQUENCE: 9

```
Asn Ala Asn Pro Asn Ala Asn Pro Asn Ala Asn Pro Asn Ala Asn Pro
1               5                   10                  15

Lys Lys Lys Lys Lys Lys Lys Lys Lys Lys Lys Lys Lys Lys
            20                  25                  30
```

Lys Lys Lys Lys Tyr
        35

<210> SEQ ID NO 10
<211> LENGTH: 45
<212> TYPE: PRT
<213> ORGANISM: Artificial Sequence
<220> FEATURE:
<223> OTHER INFORMATION: Designed peptide

<400> SEQUENCE: 10

Glu Tyr Leu Asn Lys Ile Gln Asn Ser Leu Ser Thr Glu Trp Ser Pro
1               5                   10                  15

Cys Ser Val Thr Ser Gly Asn Gly Lys Lys Lys Lys Lys Lys Lys Lys
            20                  25                  30

Lys Lys Lys Lys Lys Lys Lys Lys Lys Lys Lys Tyr
        35                  40                  45

<210> SEQ ID NO 11
<211> LENGTH: 53
<212> TYPE: PRT
<213> ORGANISM: Artificial Sequence
<220> FEATURE:
<223> OTHER INFORMATION: Designed peptide

<400> SEQUENCE: 11

Asp Pro Asn Ala Asn Pro Asn Val Asp Pro Asn Ala Asn Pro Asn Val
1               5                   10                  15

Asn Ala Asn Pro Asn Ala Asn Pro Asn Ala Asn Pro Asn Ala Asn Pro
            20                  25                  30

Lys Lys Lys Lys Lys Lys Lys Lys Lys Lys Lys Lys Lys Lys Lys Lys
        35                  40                  45

Lys Lys Lys Lys Tyr
        50

<210> SEQ ID NO 12
<211> LENGTH: 61
<212> TYPE: PRT
<213> ORGANISM: Artificial Sequence
<220> FEATURE:
<223> OTHER INFORMATION: Designed peptide

<400> SEQUENCE: 12

Asp Pro Asn Ala Asn Pro Asn Val Asp Pro Asn Ala Asn Pro Asn Val
1               5                   10                  15

Glu Tyr Leu Asn Lys Ile Gln Asn Ser Leu Ser Thr Glu Trp Ser Pro
            20                  25                  30

Cys Ser Val Thr Ser Gly Asn Gly Lys Lys Lys Lys Lys Lys Lys Lys
        35                  40                  45

Lys Lys Lys Lys Lys Lys Lys Lys Lys Lys Lys Tyr
    50                  55                  60

<210> SEQ ID NO 13
<211> LENGTH: 57
<212> TYPE: PRT
<213> ORGANISM: Artificial Sequence
<220> FEATURE:
<223> OTHER INFORMATION: Designed peptide

<400> SEQUENCE: 13

Asn Ala Asn Pro Asn Ala Asn Pro Asn Ala Asn Pro Glu Tyr Leu Asn
1               5                   10                  15

```
Lys Ile Gln Asn Ser Leu Ser Thr Glu Trp Ser Pro Cys Ser Val Thr
             20                  25                  30

Ser Gly Asn Gly Lys Lys Lys Lys Lys Lys Lys Lys Lys Lys
         35                  40                  45

Lys Lys Lys Lys Lys Lys Lys Lys Tyr
    50                  55
```

<210> SEQ ID NO 14
<211> LENGTH: 41
<212> TYPE: PRT
<213> ORGANISM: Artificial Sequence
<220> FEATURE:
<223> OTHER INFORMATION: Designed peptide

<400> SEQUENCE: 14

```
Leu Glu Phe Val Lys Gln Ile Arg Asp Ser Ile Thr Glu Glu Trp Ser
1               5                   10                  15

Gln Cys Asn Val Lys Lys Lys Lys Lys Lys Lys Lys Lys Lys Lys
             20                  25                  30

Lys Lys Lys Lys Lys Lys Lys Tyr
        35                  40
```

<210> SEQ ID NO 15
<211> LENGTH: 41
<212> TYPE: PRT
<213> ORGANISM: Artificial Sequence
<220> FEATURE:
<223> OTHER INFORMATION: Designed peptide

<400> SEQUENCE: 15

```
Lys Asn Asn Asn Asp Asp Ser Tyr Ile Pro Ser Ala Glu Lys Ile
1               5                   10                  15

Leu Glu Phe Val Lys Lys Lys Lys Lys Lys Lys Lys Lys Lys Lys
             20                  25                  30

Lys Lys Lys Lys Lys Lys Lys Tyr
        35                  40
```

<210> SEQ ID NO 16
<211> LENGTH: 57
<212> TYPE: PRT
<213> ORGANISM: Artificial Sequence
<220> FEATURE:
<223> OTHER INFORMATION: Designed peptide

<400> SEQUENCE: 16

```
Lys Asn Asn Asn Asp Asp Ser Tyr Ile Pro Ser Ala Glu Lys Ile
1               5                   10                  15

Leu Glu Phe Val Lys Gln Ile Arg Asp Ser Ile Thr Glu Glu Trp Ser
             20                  25                  30

Gln Cys Asn Val Lys Lys Lys Lys Lys Lys Lys Lys Lys Lys
         35                  40                  45

Lys Lys Lys Lys Lys Lys Lys Lys Tyr
    50                  55
```

<210> SEQ ID NO 17
<211> LENGTH: 70
<212> TYPE: PRT
<213> ORGANISM: Artificial Sequence
<220> FEATURE:
<223> OTHER INFORMATION: Designed peptide

<400> SEQUENCE: 17

-continued

```
Ser Lys Lys Lys Lys Asn Ala Asn Pro Asn Val Asp Pro Asn Ala Asn
1               5               10              15

Pro Asn Val Asp Pro Asn Ala Asn Pro Asn Val Asp Pro Asn Ala Asn
            20              25              30

Pro Asn Ala Asn Pro Asn Ala Asn Pro Asn Ala Asn Pro Asn Ala Asn
            35              40              45

Pro Lys Lys Lys Lys Lys Lys Lys Lys Lys Lys Lys Lys Lys
    50              55              60

Lys Lys Lys Lys Lys Tyr
65              70
```